US008278427B2

(12) United States Patent
Yanagawa et al.

(10) Patent No.: US 8,278,427 B2
(45) Date of Patent: Oct. 2, 2012

(54) MOLECULE FOR ASSIGNING GENOTYPE TO PHENOTYPE AND COMPONENTS THEREOF AS WELL AS METHOD FOR CONSTRUCTING ASSIGNING MOLECULE AND METHOD FOR UTILIZING ASSIGNING MOLECULE

(75) Inventors: Hiroshi Yanagawa, Yokohama (JP); Etsuko Miyamoto, Yokohama (JP); Hideaki Takashima, Yokohama (JP)

(73) Assignee: KEIO University, Tokyo (JP)

( * ) Notice: Subject to any disclaimer, the term of this patent is extended or adjusted under 35 U.S.C. 154(b) by 1237 days.

(21) Appl. No.: 10/460,467

(22) Filed: Jun. 13, 2003

(65) Prior Publication Data

US 2004/0018536 A1 Jan. 29, 2004

Related U.S. Application Data

(63) Continuation of application No. PCT/JP01/10862, filed on Dec. 11, 2001.

(30) Foreign Application Priority Data

Dec. 14, 2000 (JP) .................................. 2000-380562

(51) Int. Cl.
*C07H 21/04* (2006.01)
*C12N 15/00* (2006.01)
*A61K 31/70* (2006.01)
(52) U.S. Cl. .................... 536/23.1; 536/24.2; 435/320.1
(58) Field of Classification Search .................. None
See application file for complete search history.

(56) References Cited

U.S. PATENT DOCUMENTS

| | | | | |
|---|---|---|---|---|
| 5,843,701 | A | 12/1998 | Gold et al. | 435/68.1 |
| 5,942,433 | A * | 8/1999 | Vinson et al. | 435/320.1 |
| 5,958,731 | A * | 9/1999 | Yue et al. | 435/69.1 |
| 6,207,446 | B1 | 3/2001 | Szostak et al. | 435/287.2 |
| 6,214,553 | B1 | 4/2001 | Szostak et al. | 435/6 |
| 6,258,558 | B1 | 7/2001 | Szostak et al. | 435/69.1 |
| 6,261,804 | B1 | 7/2001 | Szostak et al. | 435/69.1 |
| 6,281,344 | B1 | 8/2001 | Szostak et al. | 536/23.1 |
| 6,361,943 | B1 | 3/2002 | Yanagawa et al. | 435/6 |
| 6,365,346 | B1 * | 4/2002 | Patel et al. | 435/6 |
| 6,429,300 | B1 * | 8/2002 | Kurz et al. | 536/23.1 |
| 6,518,018 | B1 | 2/2003 | Szostak et al. | 435/6 |
| 2002/0072087 | A1 | 6/2002 | Yanagawa et al. | 435/68.1 |
| 2003/0002230 | A1 | 1/2003 | Dee et al. | 360/324.12 |
| 2003/0022230 | A1 | 1/2003 | Yanagawa et al. | 435/6 |

FOREIGN PATENT DOCUMENTS

| | | |
|---|---|---|
| DE | 196 46 372 | 6/1997 |
| JP | 98/016636 * | 4/1998 |
| WO | 95/02684 | 1/1995 |
| WO | 95/09010 | 4/1995 |
| WO | 95/11922 | 5/1995 |
| WO | 96/22391 | 7/1996 |
| WO | 98/16636 | 4/1998 |
| WO | 98/31700 | 7/1998 |
| WO | 00/32823 | 6/2000 |
| WO | 01/16600 | 3/2001 |

OTHER PUBLICATIONS

Uberlacker et al (Vector with rare-cutter restriction enzyme sites for expression of open reading frames in transgenic plants. Molecular Breeding, 1996. 2:293-295).*
Romaniuk et al. The effect of acceptor oligoribonucleotide sequence on the T4 RNA ligase reaction. Eur. J. Biochem. 125:639-643, 1982.*
Hinton et al. T4 RNA ligase joins 2'-Deoxyribonucleoside 3',5'-bisphosphates to oligodeoxyribonucleotides. Biochemistry 17:5091-5097, 1978.*
Sambrook et al. In: Molecular Cloning, Second edition, ColdSpring Harbor Laboratory Press, 5.56-5,57, 1989.*
R. Liu et al., "Optimized synthesis of RNA-protein fusions for in vitro protein selection.", Methods Enzymol., vol. 318, Jul. 2000, pp. 268-293.
N. Nemoto et al., "In vitro virus: bonding of mRNA bearing puromycin at the 3'-terminal end to the C-terminal end of its encoded protein on the ribosome in vitro.", FEBS Letter, vol. 414, No. 2, 1997, pp. 405-408.
Fusimi et al., "Role of the Virus-Type Strategy in Encoded Molecular Evolution", Progress in Biophysics & Molecular Biology, vol. 65, Suppl. 1, p. 64, Aug. 1996.
S. Brenner et al., "Encoded Combinatorial Chemistry", Proc. Natl. Acad. Sci., vol. 89, pp. 5381-5388, Jun. 1992.
C. Tung et al., "Dual-Specificity Interaction of HIV-1 TAR RNA with Tat Peptide-Oligonucleotide Conjugates", Bioconjugate Chem., vol. 6, pp. 292-295, 1995.
"Identification of the motifs within the tobacco mosaic virus 5'-leader responsible for enhancing translation", Gaille, Daniel R. and Walbot, Virginia, *Nucleic Acids Research*, vol. 20, No. 17, pp. 4631-4638. Oxford University Press (1992).
M. Kurz et al., "Psoralen-Photo-Crosslinked mRNA-Puromycin Conjugates: A Novel Template for the Rapid and Pa Preparation of mRNA-Protein Fusions", Nucleic Acids Research, vol. 28, No. 18, 2000, p. 883 (I-V).
T. So et al., "The Molecular Weight Ratio of Monomethoxypolyethylene Glycol (mPEG) to Protein Determines the Immunotolerogenicity of mPEG Proteins", Protein Engineering, vol. 12, No. 8, 1999, pp. 701-705.

* cited by examiner

*Primary Examiner* — Quang Nguyen
(74) *Attorney, Agent, or Firm* — Wenderoth, Lind & Ponack, L.L.P.

(57) ABSTRACT

An assigning molecule obtained by ligating a genotype molecule to a phenotype molecule by transpeptidation, wherein the genotype molecule is constructed by bonding (a) a spacer molecule comprising a donor region which can be bonded to a 3'-terminal end of nucleic acid, a PEG region bonded to the donor region and a peptide acceptor region which is bonded to the PEG region, to (b) a 3' end of a nucleic acid comprising a 5' untranslated region comprising a transcription promoter and a translation enhancer; an ORF region which comprises a polyA sequence and which is bonded to the 3'-terminal side of the 5' untranslated region; and a 3'-terminal region that is bonded to the 3'-terminal side of the ORF region.

6 Claims, 11 Drawing Sheets

Transcription promoter
SP6: ATTTAGGTGACACTATA
Translation enhancer
O29(Omega29): GAAACAACAACAACAAACAAACAACAACAAAATG

Affinity tag
Flag-tag: GACTACAAGGACGATGACGACAAG
XhoI: CTCGAG
PolyA sequence: An(n=2 bp~)

SEQUENCE LISTING

<160> NUMBER OF SEQ ID NOS: 16

<210> SEQ ID NO 1
<211> LENGTH: 378

```
<212> TYPE: DNA
<213> ORGANISM: Artificial Sequence
<220> FEATURE:
<223> OTHER INFORMATION: Synthetic Construct

<400> SEQUENCE: 1
atggctagca tgactggtgg acagcaaatg ggtgcggccg cgccggagat gccgggagag      60
acgccgcccc tgtccctat cgacatggag tctcaggagc ggatcaaggc agagaggaag      120
cgcatgagga accgcattgc cgcctccaag tgccggaaaa ggaagctgga gcggatcgct      180
cggctagagg aaaaagtgaa aaccttgaaa gcgcaaaact ccgagctggc atccacggcc      240
aacatgctca gggaacaggt ggcacagctt aagcagaaag tcatgaacca cgttaacagt      300
gggtgccaac tcatgctaac gcagcagttg caaacgttta accgcggga ctacaaggac      360 gatgacgaca agctcgag                                                    378

<210> SEQ ID NO 2
<211> LENGTH: 76
<212> TYPE: DNA
<213> ORGANISM: Artificial Sequence
<220> FEATURE:
<223> OTHER INFORMATION: Synthetic Construct

<400> SEQUENCE: 2
atttaggtga cactatagaa caacaacaac aacaaacaac aacaaaatgg ctagcatgac      60
tggtggacag caaatg                                                       76

<210> SEQ ID NO 3
<211> LENGTH: 76
<212> TYPE: DNA
<213> ORGANISM: Artificial Sequence
<220> FEATURE:
<223> OTHER INFORMATION: Synthetic Construct

<400> SEQUENCE: 3
taatacgact cactataggg caacaacaac aacaaacaac aacaaaatgg ctagcatgac      60
tggtggacag caaatg                                                       76

<210> SEQ ID NO 4
<211> LENGTH: 73
<212> TYPE: DNA
<213> ORGANISM: Artificial Sequence
<220> FEATURE:
<223> OTHER INFORMATION: Synthetic Construct

<400> SEQUENCE: 4
taatacgact cactataggg agaccacaac ggtttcccat ttaggtgaca ctatagaata      60
cacggaattc gcg                                                          73

<210> SEQ ID NO 5
<211> LENGTH: 73
<212> TYPE: DNA
<213> ORGANISM: Artificial Sequence
<220> FEATURE:
<223> OTHER INFORMATION: Synthetic Construct

<400> SEQUENCE: 5
taatacgact cactataggg agaccacaac ggtttcccat ttaggtgaca ctatagaata      60
cacggaattc gcg                                                          73

<210> SEQ ID NO 6
<211> LENGTH: 72
```

```
<212> TYPE: DNA
<213> ORGANISM: Artificial Sequence
<220> FEATURE:
<223> OTHER INFORMATION: Synthetic Construct

<400> SEQUENCE: 6
taatacgact cactataggg acaattacta tttacaatta caatggctag catgactggt    60
ggacagcaaa tg                                                       72

<210> SEQ ID NO 7
<211> LENGTH: 71
<212> TYPE: DNA
<213> ORGANISM: Artificial Sequence
<220> FEATURE:
<223> OTHER INFORMATION: Synthetic Construct

<400> SEQUENCE: 7
taatacgact cactataggg agaccacaac ggtttcccgc cgccaccatg gctagcatga    60
ctggtggaca g                                                        71

<210> SEQ ID NO 8
<211> LENGTH: 36
<212> TYPE: DNA
<213> ORGANISM: Artificial Sequence
<220> FEATURE:
<223> OTHER INFORMATION: Synthetic Construct

<400> SEQUENCE: 8
ttttttttct cgagcttgtc gtcatcgtcc ttgtag                              36

<210> SEQ ID NO 9
<211> LENGTH: 28
<212> TYPE: DNA
<213> ORGANISM: Artificial Sequence
<220> FEATURE:
<223> OTHER INFORMATION: Synthetic Construct

<400> SEQUENCE: 9
ctcgagcttg tcgtcatcgt ccttgtag                                       28

<210> SEQ ID NO 10
<211> LENGTH: 38
<212> TYPE: DNA
<213> ORGANISM: Artificial Sequence
<220> FEATURE:
<223> OTHER INFORMATION: Synthetic Construct

<400> SEQUENCE: 10
ttttttttct cgaccttgtc gtcatcgtcc ttgtagtc                            38

<210> SEQ ID NO 11
<211> LENGTH: 38
<212> TYPE: DNA
<213> ORGANISM: Artificial Sequence
<220> FEATURE:
<223> OTHER INFORMATION: Synthetic Construct

<400> SEQUENCE: 11
ttttttttgt cgagcttgtc gtcatcgtcc ttgtagtc                            38

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct
```

```
<400> SEQUENCE: 12 tttttttct tgtcgtcatc gtccttgtag tcccg                                    35

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13
gactacaagg acgatgacga caag                                               24

<210> SEQ ID NO 14
<211> LENGTH: 17
<212> TYPE: DNA
<213> ORGANISM: Artificial Sequence
<220> FEATURE:
<223> OTHER INFORMATION: Synthetic Construct

<400> SEQUENCE: 14
atttaggtga cactata                                                       17

<210> SEQ ID NO 15
<211> LENGTH: 32
<212> TYPE: DNA
<213> ORGANISM: Artificial Sequence
<220> FEATURE:
<223> OTHER INFORMATION: Synthetic Construct

<400> SEQUENCE: 15
gaacaacaac aacaacaaac aacaacaaaa tg                                      32

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
gactacaagg acgatgacga caag                                               24
```

MOLECULE FOR ASSIGNING GENOTYPE TO PHENOTYPE AND COMPONENTS THEREOF AS WELL AS METHOD FOR CONSTRUCTING ASSIGNING MOLECULE AND METHOD FOR UTILIZING ASSIGNING MOLECULE

This application is 53(b) continuation application of International Application No. PCT/JP01/10862 filed Dec. 11, 2001.

TECHNICAL FIELD

With the advancement of genetic engineering, it has become possible to readily construct biopolymers such as nucleotides and peptides of which sequences are given, and in the protein engineering, it is being attempted to elucidate molecular structural and functional correlations as an approach for understanding biopolymer functions and intermolecular interactions. However, it is difficult to theoretically approach three-dimensional structures of them due to the diversity and complexity of the structures, and the attempt remains at the stage of modifying several residues in an active site and observing resultant changes in the structure and functions. In the evolutionary molecular engineering (Fushimi, J. (1991) Kagaku, 61, 333-340; Fushimi, J. (1992) Koza Shinka, vol. 6, University of Tokyo Press), which has been recently highlighted, this difficult approach is not required, but selection pressure is applied based on a function to evolve proteins etc. in vitro or to detect interactions between proteins or between a nucleic acid and a protein and analyze their networks (Miyamoto, E. & Yanagawa, H. (2000) Series: Post-Sequence Genome Science 3: Proteomics, pp. 136-156; Miyamoto, E. & Yanagawa, H. (2001) Tanpakushitsu Kakusan Koso, 46(1): 1-10).

The evolutionary molecular engineering of proteins based on evolutionary molecular engineering of RNA, which appeared in the 1990s, primarily aims at searching a vast sequence space, which can no way be contemplated in the conventional protein engineering, to select optimum sequences therefrom. As is symbolized by the fact that we still find "screening" useful even now in selection of useful proteins, molecular designing based on the structural theory is imperfect at present, and thus evolutionary techniques have a practical value as more efficient techniques.

The evolutionary molecular engineering also enables detection of intermolecular interactions and analysis of the networks thereof by centering functions, and in particular, it is expected to be applied to functional analyses of genomes, which are increasingly becoming important in recent years (Miyamoto, E. & Yanagawa, H. (2000) Series Post-Sequence Genomic Science 3: Proteomics, pp.136-156; Miyamoto, E. & Yanagawa, H. (2001) Tanpakushitsu Kakusan Koso, 46(1), pp.1-10). Thus, the evolutionary molecular engineering and post-genome functional analyses of proteins can of course be applied to biotechnology such as utilization of biochips, biosensors and enzymes as industrial catalysts by modification of functional biopolymers and creation of biopolymers having functions which cannot be found in living organisms, and it can also be utilized in many industrial areas such as medicine, food, energy and environment including preparation of drugs by discovery of important bioenzymes etc. based on analysis of networks of interactions between proteins.

BACKGROUND ART

The evolutionary molecular engineering is a science aiming at constructing a system that progressively evolves by repetition of three unit operations, "mutation", "selection" and "amplification" utilizing the Darwin's evolution mechanism and applying the system in engineering. The evolutionary molecular engineering was theoretically proposed by Eigen et al. in 1984, and it is new biotechnology molecular design of functional biopolymers is performed by in vitro high-speed molecular evolution, that is, by investigating mechanisms of adaptive locomotion of biopolymers in a sequence space and optimizing them in laboratory experiments (Fushimi J. (1991) Kagaku, 61, 333-340; Fushimi J. (1992) Koza Shinka, vol. 6, University of Tokyo Press).

As one of important elemental techniques in the evolutionary molecular engineering, "assigning of genotype to phenotype" can be mentioned. The following three types of the "assigning of genotype to phenotype" are frequently adopted in the natural world or evolutionary molecular engineering (Fushimi J. (1999) Kagaku to Seibutsu, 37, 678-684):

(a) the ribozyme type in which a portion corresponding to a genotype and a portion corresponding to a phenotype are carried on the same molecule;

(b) the virus type in which a portion corresponding to a genotype and a portion corresponding to a phenotype form a complex; and (c) the cell type in which a portion corresponding to a genotype and a portion corresponding to a phenotype are contained in a single compartment.

The evolutionary molecular engineering of RNA is of (a) the ribozyme type, and (b) the virus type or (c) the cell type is contemplated for the evolutionary molecular engineering of proteins. In the 1990s, RNA evolutionary molecular engineering was developed by Joyce and Szostak et al. (Joyce, G. F. (1989) Gene, 82, 83; Szostak, J. W. & Ellington A. D. (1990) Nature, 346, 818), and in vitro experimental RNA systems (in vitro selection systems) utilizing (a) the ribozyme-type assigning technique were proposed. Subsequently, the in vitro virus method (Nemoto, N., Miyamoto-Sato, E., Yanagawa, H. (1997) FEBS Lett., 414, 405; Yanagawa, H., Nemoto, N., Miyamoto, E. (1998) WO98/16636), RNA-peptide fusion method (Roberts, R. W., Szostak, J. W. (1997) Proc. Natl. Acad. Sci. USA, 94, 12297), STABLE method (Doi, N. & Yanagawa, H. (1999) FEBS Lett., 457, 227) and so forth have been reported as in vitro experimental systems for proteins (in vitro selection systems) utilizing the virus-type technique of assigning a genotype to a phenotype in the protein evolutionary molecular engineering. In addition, various techniques of the virus-type evolutionary molecular engineering have been proposed so far including the phage display (Smith, G. P. (1985) Science, 228, 1315-1317; Scott, J. K. & Smith, G. P. (1990) Science, 249, 386-390), polysome display (Mattheakis, L. C. et al. (1994) Proc. Natl. Acad. Sci. USA, 91, 9022-9026), library with encoding tags (Brenner, S. & Lerner, R. A. (1992) Proc. Natl. Acad. Sci. USA, 89, 5381-5383), Cellstat (Husimi, Y. et al. (1982) Rev. Sci. Instrum., 53, 517-522) and so forth.

The sequence space size, that is, size of a library, searchable in the evolutionary molecular engineering and post-genome functional analysis is important. As for the virus-type assigning molecules, the size of a library using is limited by a host cell when existing virus is utilized as in the case of phage display, since the virus parasites a cell. One the other hand, since the virus-type assigning molecules can be constructed in vitro in the aforementioned in vitro virus method (Nemoto, N., Miyamoto-Sato, E., Yanagawa, H. (1997) FEBS Lett., 414, 405; Yanagawa, H., Nemoto N. & Miyamoto E. (1998) WO98/16636), RNA-peptide fusion method (Roberts, R. W., Szostak, J. W. (1997) Proc. Natl. Acad. Sci. USA, 94, 12297) and so forth, these methods are theoretically expected as global searching methods for a sequence space comparable with the ribozyme-type technique. Further, in the evolutionary molecular engineering, not only the size of searchable sequence space, but also its diversity is important. The polysome display method (Mattheakis, L. C. & Dower, W. J. (1995) WO95/11922) is known, and this technique is suitable for a peptide with a short chain length, since nucleic acid and a protein are bonded by a noncovalent bond via ribosome in this technique. However, when the chain length becomes long like a protein, handling thereof becomes problematic, that is, diversity of library is limited due to the limited chain length of the genotype. As also for this problem, it is theoretically considered that no limitation is imposed on the chain length to be handled in the virus-type assigning molecules for the in vitro virus method, RNA-peptide fusion method and so forth. However, in order to actually construct a large-scale library and handle genotypes with a long chain length, several problems must be solved.

As described above, in principle, a large-scale library can be constructed by using virus-type assigning molecules in vitro as in the in vitro virus method, RNA-peptide fusion method and so forth. In practice, however, the size of the library depends on the efficiency of construction of the virus-type assigning molecules. The virus-type assigning molecules are constructed by bonding a spacer containing puromycin to a nucleic acid sequence containing protein information using a certain method to construct a genotype molecule and ligating it to a phenotype molecule (protein) on ribosome in a cell-free translation system. In this case, since a genotype molecule to which a spacer is not bonded, that is, a genotype molecule without puromycin, cannot be ligated to a phenotype molecule, the spacer binding efficiency determines the size of library. For example, in the RNA-peptide fusion method, a sprint and DNA ligase are used to ligate a DNA spacer. However, 1 random residue that does not exist in a template may be often added to the 3'-terminal end of the genotype molecule at the time of transcription. Thus, the sequence of the molecule does not match the sprint sequence, and hence ligation efficiency becomes poor. Accordingly, the sprint is modified, but much labor and cost are required. Further, in the in vitro virus method, RNA ligase is used to ligate a DNA spacer. Since RNA ligase does not require a sprint, it has no such a problem as that of the DNA ligase. However, it is known that RNA ligase originally has lower enzymatic activity compared with DNA ligase, and its ligation efficiency is also poor.

So far, in both of the in vitro virus method and the RNA-peptide fusion method, the usable cell-free translation system is limited to a rabbit reticulocyte cell-free translation system. Further, the virus-type assigning molecule construction efficiency in the rabbit reticulocyte cell-free translation system has remained as low as only 1% or lower (Roberts, R. W. & Szostak, J. W. (1997) Proc. Natl. Acad. Sci. USA, 94, 12297) or 10% or lower (Nemoto, N., Miyamoto-Sato, E., Yanagawa, H. (1997) FEBS Lett., 414, 405) of mRNA templates (genotype molecule) added to the cell-free translation system. Although the efficiency is increased to 20 to 40% by treatment after translation in the RNA-peptide fusion method (Liu, R., Barrick, E., Szoztak, J. W., Roberts, R. W. (2000) Methods in Enzymology, 318, 268-293), this requires much labor and time such as ordinary translation followed by addition of magnesium ions ($Mg^{2+}$) and potassium ions ($K^+$) and incubation at –20° C. for 2 days. In the rabbit reticulocyte cell-free translation system, in addition to the low assigning efficiency, mRNA stability is low, and therefore mRNA with a long chain cannot be handled. In contrast, in a wheat germ cell-free translation system, mRNA stability is favorable, and hence mRNA with a long chain can be handled. Therefore, it is desirable that a virus-type assigning molecule can be constructed on ribosome in the wheat germ cell-free translation system, but this has not been realized so far.

Among other factors determining the construction efficiency of virus-type assigning molecules, the most important one is the difference in translation efficiency of the genotype molecule. This can be expected to largely depend on sequences of a transcription promoter and a translation enhancer in the 5' untranslated region (5' UTR), 3'-end side sequence and so forth of the genotype molecule. However, there has been no report on examination of the relationship between the translation efficiency and the virus-type assigning molecule construction efficiency.

DISCLOSURE OF THE INVENTION

An object of the present invention is to improve the scale and diversity of a library, which are important in the evolutionary molecular engineering and post-genome functional analysis, and to improve efficiency of construction of assigning molecules in order to achieve the above object. Further, another object of the present invention is to achieve higher efficiency and simplification of each step of ligation and assigning translation. Further, another object of the present invention is to construct a virus-type assigning molecule in a wheat germ cell-free translation system to enable mass synthesis and handling of long genotype molecules, which are advantages of use of wheat germ, and thereby establish a foundation for constructing a large library with high diversity in both of the evolutionary molecular engineering and genome functional analysis.

The inventors of the present invention earnestly conducted investigations to achieve the aforementioned objects. As a result, they found that the construction of the assigning molecule, which had been limited to the rabbit reticulocyte cell-free translation system so far, could be realized in the wheat germ cell-free translation system, the construction efficiency of the assigning molecules was improved, and a large-scale library with high diversity could be realized by improving a spacer containing puromycin (referred to as "spacer portion" hereinafter) and a nucleotide sequence containing protein information (referred to as "coding portion" hereinafter) in such an assigning molecule as shown in FIG. 1. The expression "an assigning molecule" as shown in FIG. 1 used herein means an assigning molecule constructed by bonding a spacer portion containing puromycin to a coding portion by a certain method to obtain a genotype molecule and ligating it to a phenotype molecule (referred to as "decoded portion" hereinafter) on a ribosome in a cell-free translation system.

Accordingly, the present invention provides the followings.

(1) A spacer molecule comprising a donor region which can be bonded to a 3'-terminal end of nucleic acid, a PEG region that is bonded to the donor region and comprises polyethylene glycol as a main component and a peptide acceptor region which is bonded to the PEG region and comprises a group which can be bonded to a peptide by transpeptidation.

(2) The spacer molecule according to (1), wherein the peptide acceptor region comprises puromycin or a derivative thereof, or puromycin or a derivative thereof and one or two residues of deoxyribonucleotides or ribonucleotides.

(3) The spacer molecule according to (1) or (2), which comprises at least one function-imparting unit between the donor region and the PEG region.

(4) The spacer molecule according to (3), wherein the function-imparting unit is at least one residue of functionally modified deoxyribonucleotide or ribonucleotide.
(5) A coding molecule, which is a nucleic acid comprising a 5' untranslated region comprising a transcription promoter and a translation enhancer; an ORF region which is bonded to the 3'-terminal side of the 5' untranslated region and encodes a protein; and a 3'-terminal region which is bonded to the 3'-terminal side of the ORF region and comprises a polyA sequence and a sequence which a restriction enzyme XhoI recognizes on the 5'-terminal side of the polyA sequence.
(6) The coding molecule according to (5), wherein the transcription promoter is a promoter of SP6 RNA polymerase.
(7) The coding molecule according to (5) or (6), wherein the translation enhancer is a part of the TMV omega sequence of tobacco mosaic virus (O29).
(8) The coding molecule according to any one of (5) to (7), which comprises an affinity tag sequence in a portion downstream from the ORF region.
(9) The coding molecule according to (8), wherein the affinity tag sequence is a Flag-tag sequence, which is a tag for affinity separation and analysis based on an antigen-antibody reaction.
(10) A genotype molecule constructed by bonding a 3'-terminal end of a coding molecule which is a nucleic acid comprising a 5' untranslated region comprising a transcription promoter and a translation enhancer; an ORF region which is bonded to the 3'-terminal side of the 5' untranslated region and encodes a protein; and a 3'-terminal region which is bonded to the 3'-terminal side of the ORF region and comprises a polyA sequence, to the donor region of the spacer molecule as defined in any one of (1) to (4).
(11) The genotype molecule according to (10), wherein the transcription promoter is a promoter of SP6 RNA polymerase.
(12) The genotype molecule according to (10) or (11), wherein the translation enhancer is a part of the TMV omega sequence of tobacco mosaic virus (O29).
(13) The genotype molecule according to any one of (10) to (12), wherein the 3'-terminal end sequence comprises a sequence which a restriction enzyme XhoI recognizes on the 5'-terminal end side of the polyA sequence.
(14) The genotype molecule according to any one of (10) to (13), which comprises an affinity tag sequence in a portion downstream from the ORF region.
(15) The genotype molecule according to (14), wherein the affinity tag sequence is a Flag-tag sequence, which is a tag for affinity separation and analysis based on an antigen-antibody reaction.
(16) A method for constructing a genotype molecule, which comprises bonding (a) a 3'-terminal end of a coding molecule which is RNA comprising a 5' untranslated region comprising a transcription promoter and a translation enhancer; an ORF region which is bonded to the 3'-terminal side of the 5' untranslated region and encodes a protein; and a 3'-terminal region which is bonded to the 3'-terminal side of the ORF region and comprises a polyA sequence, to (b) the donor region of the spacer molecule as define in any one of (1) to (4), which comprises RNA, by using RNA ligase in the presence of free polyethylene glycol having the same molecular weight as that of polyethylene glycol constituting the PEG region in the spacer molecule.
(17) An assigning molecule constructed by ligating the genotype molecule as defined in any one of (10) to (15) to a phenotype molecule which is a protein encoded by the ORF region in the genotype molecule, by transpeptidation.
(18) A method for constructing an assigning molecule, which comprises translating the genotype molecule as defined in any one of (10) to (15) in a cell-free translation system to ligate the genotype molecule to a phenotype molecule which is a protein encoded by the ORF region in the genotype molecule, by transpeptidation.
(19) The method according to (18), wherein the cell-free translation system is a wheat germ cell-free translation system.
(20) The method according to (18), wherein the cell-free translation system is a rabbit reticulocyte cell-free translation system.
(21) A method for screening a nucleotide sequence encoding a protein which acts on a target substance, which comprises measuring an interaction between a decoded portion of an assigning molecule and the target substance by using a library comprising a plurality of the assigning molecules as defined in (17), among which at least a part of the assigning molecules have different sequences of the ORF regions in their coding portions, and detecting the nucleotide sequence of the coding portion of the assigning molecule exhibiting the interaction.

BEST MODE FOR CARRYING OUT THE INVENTION

In the present specification, the term "assigning molecule" means a molecule that assigns a genotype to a phenotype. The assigning molecule is constructed by bonding a genotype molecule comprising nucleic acid having a nucleotide sequence that reflects a genotype, to a phenotype molecule comprising a protein involved in expression of a phenotype. The genotype molecule is constructed by bonding a coding molecule that has the nucleotide sequence reflecting a genotype in such a form that the nucleotide sequence can be translated, to a spacer portion.

A portion derived from the phenotype molecule, a portion derived from the spacer molecule and a portion derived from the coding molecule in the assigning molecule are referred to as a decoded portion, a spacer portion and a coding portion, respectively. Further, a portion derived from the spacer molecule and a portion derived from the coding molecule in the genotype molecule are referred to as a spacer portion and a coding portion, respectively.

Figure 1:
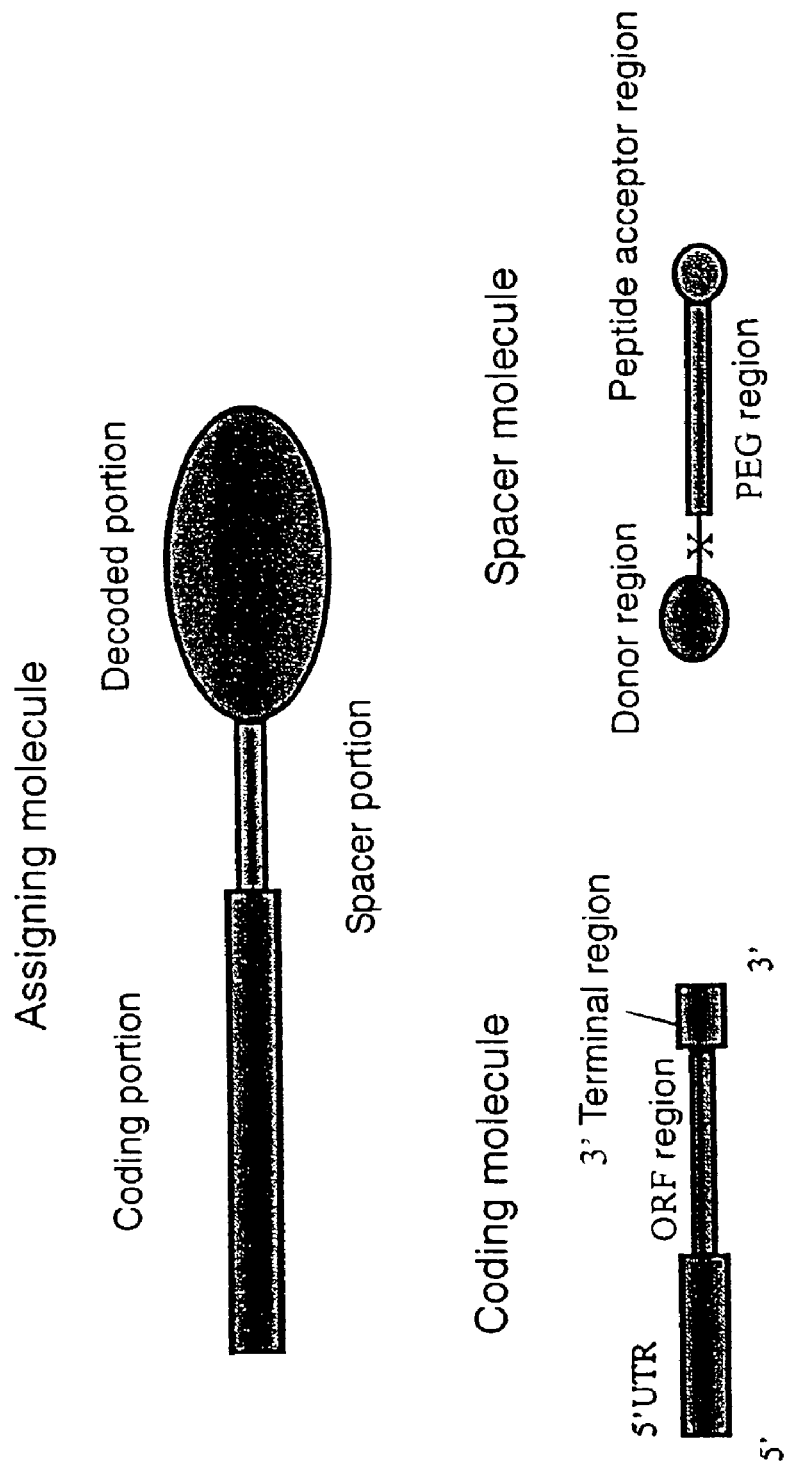
FIG. 1 is a schematic view showing structures of the assigning molecule, the spacer molecule and the coding molecule of the present invention.

FIG. 1 shows schematic constitutions of exemplary assigning molecule, spacer molecule and coding molecule of the present invention. This assigning molecule comprises a spacer containing puromycin (referred to as "spacer portion") and a nucleotide sequence reflecting codes of a phenotype (referred to as "coding portion"). This assigning molecule is constructed by bonding the spacer portion containing puromycin to the coding molecule by a certain method to obtain a genotype molecule, and ligating the genotype molecule to a phenotype molecule on a ribosome in a cell-free translation system. The spacer molecule comprises a PEG region containing polyethylene glycol as a main component; a CCA region containing at least puromycin, or puromycin and DNA and/or RNA 1 or more residues; a donor region containing DNA and/or RNA of at least 1 residue; and further a function-imparting unit (X) comprising functionally modified DNA and/or RNA of at least 1 residue. The coding molecule comprises a 3'-terminal region that contains a polyA sequence of DNA and/or RNA comprising a sequence of a part of a decoded portion; 5' UTR that comprises DNA and/or RNA and contains a transcription promoter and a translation enhancer; and further an ORF region mainly comprising the sequence of the phenotype molecule.

<1> Spacer Molecule of the Present Invention

The spacer molecule of the present invention comprises a donor region that can be bonded to a 3'-terminal end of nucleic acid, a PEG region that is bonded to the donor region and comprises polyethylene glycol as a main component, and a peptide acceptor region that is bonded to the PEG region and comprises a group that can be bonded to a peptide by transpeptidation.

The donor region that can be bonded to the 3'-terminal end of nucleic acid usually comprises 1 or more nucleotides. The number of nucleotides is usually 1 to 15, preferably 1 to 2. The nucleotides may be ribonucleotides or deoxyribonucleotides.

The sequence of the 5'-terminal end of the donor region determines ligation efficiency. In order to ligate the coding portion and the spacer portion, at least 1 or more residues need to be contained. For the acceptor having the polyA sequence, at least 1 residue of dC (deoxycytidylic acid) or 2 residues of dCdC (dideoxycytidylic acid) are preferred. The type of the nucleotide is more preferred in the order of C>U or T>G>A.

The PEG region comprises polyethylene glycol as a main component. The expression "comprising as a main component" used herein means that the total number of nucleotides contained in the PEG region is 20 bp or less, or the average molecular weight of polyethylene glycol is 400 or more. Preferably, it means that the total number of nucleotides is 10 bp or less, or the average molecular weight of polyethylene glycol is 1000 or more.

The average molecular weight of polyethylene glycol in the PEG region is usually 400 to 30,000, preferably 1,000 to 10,000, more preferably 2,000 to 8,000. When the molecular weight of polyethylene glycol is less than about 400, a post-assigning translation treatment may be needed after the assigning translation of the genotype molecule containing a spacer portion derived from such a spacer molecule (Liu, R., Barrick, E., Szostak, J. W., Roberts, R. W. (2000) Methods in Enzymology, 318, 268-293). However, when PEG having a molecular weight of 1000 or more, more preferably 2000 or more is used, high efficiency assigning can be achieved only through the assigning translation, and therefore the post-translation treatment becomes unnecessary. Further, as the molecular weight of polyethylene glycol increases, the stability of the genotype molecule tends to increase and is favorable particularly with PEG having a molecular weight of 1000 or more. On the other hand, the genotype molecule may become unstable with PEG having a molecular weight of 400 or less, of which properties are not so different from those of a DNA spacer.

The peptide acceptor region is not particularly limited so long as it can be bonded to the C-terminal of a peptide. For example, puromycin, 3'-N-aminoacylpuromycin aminonucleoside (PANS-amino acid) such as PANS-Gly of which amino acid portion is glycine, PANS-Val of which amino acid portion is valine and PANS-Ala of which amino acid portion is alanine and PANS-total amino acids of which amino acid portion corresponds to the total amino acids can be utilized. Further, 3'-N-aminoacyladenosine aminonucleoside (AANS-amino acid) bonded with an amide bond formed as a result of condensation of an amino group of 3'-aminoadenosine and a carboxyl group of an amino acid as a chemical bond such as AANS-Gly of which amino acid portion is glycine, AANS-Val of which amino acid portion is valine and AANS-Ala of which amino acid portion is alanine and AANS-total amino acids of which amino acid portion corresponds to the total amino acids can be utilized. Further, nucleoside, a bonding product of nucleoside and amino acid via an ester bond or the like can be utilized. In addition, any substance having a bonding scheme that can chemically bond a nucleoside or a substance having a chemical structure similar to that of nucleoside and an amino acid or a substance having a chemical structure similar to that of amino acid can be utilized.

The peptide acceptor region preferably comprises puromycin or a derivative thereof, or puromycin or a derivative thereof and 1 or 2 residues of deoxyribonucleotides or ribonucleotides. The term "derivative" used herein means a derivative that can be bonded to the C-terminal of peptide in a protein translation system. The puromycin derivatives are not limited to those having a complete puromycin structure, and include those lacking a part of the puromycin structure. Specific examples of the puromycin derivatives include PANS-amino acid, AANS-amino acid and so forth.

Although it is sufficient that the peptide acceptor region is constituted by puromycin alone, it preferably has a nucleotide sequence comprising 1 or more residues of DNA and/or RNA on the 5'-terminal side. Examples of the sequences include dC-puromycin and rC-puromycin, and dCdC-puromycin, rCrC-puromycin, rCdC-puromycin, dCrC-puromycin and so forth are more preferred. The CCA sequences that imitate the 3'-terminal end of aminoacyl-tRNA (Philipps, G. R. (1969) Nature, 223, 374-377) are suitable. The type of nucleotide is more preferred in the order of C>U or T>G>A.

The spacer molecule preferably contains at least one function-imparting unit between the donor region and the PEG region. The function-imparting unit preferably comprises at least 1 residue of functionally modified deoxyribonucleotide or ribonucleotide. For example, as a functionally modified substance, those having various separation tags such as a fluorescent substance, biotin or His-tag shown in FIG. 2 introduced can be used.

Figure 2:
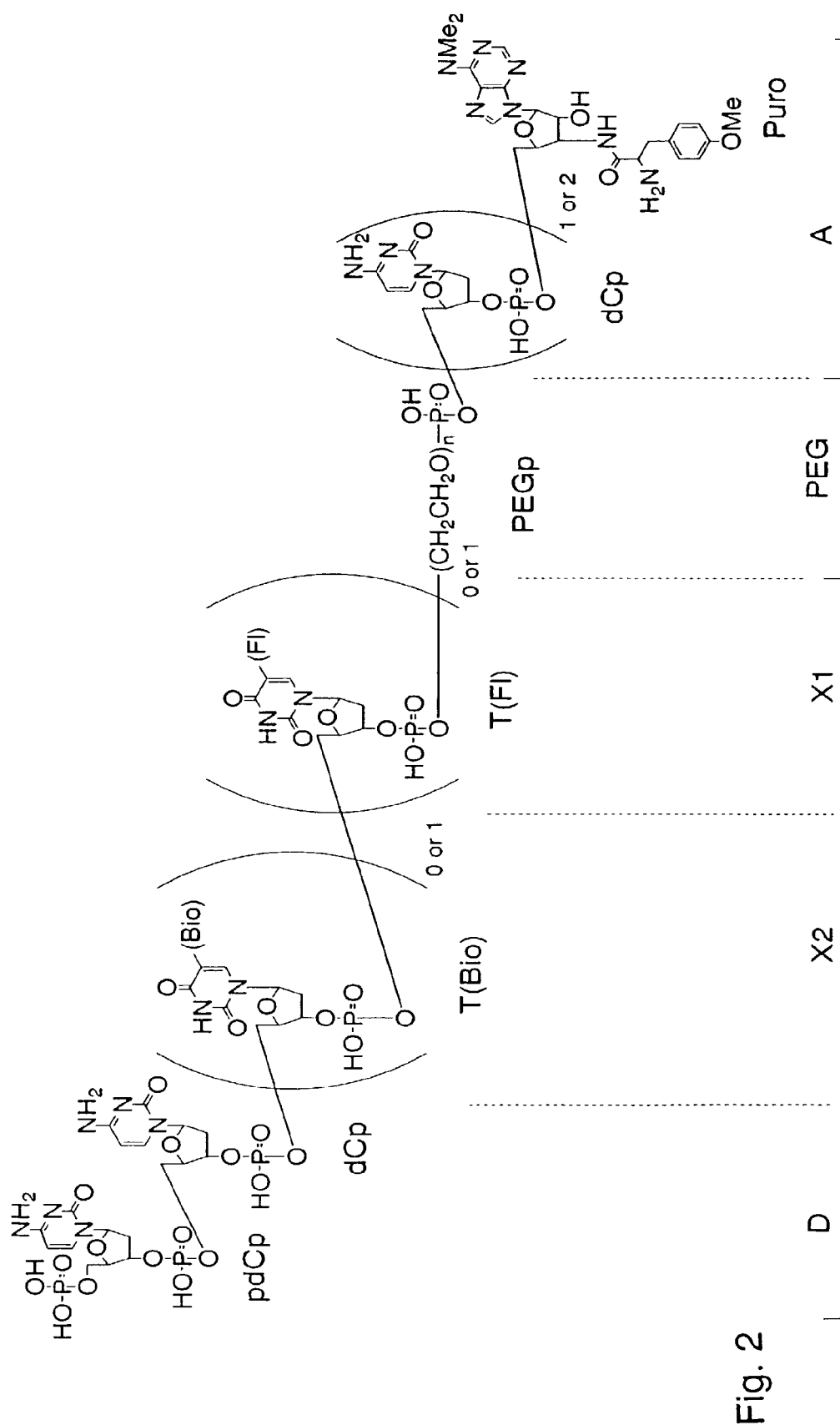
FIG. 2 shows a detailed constitution of an exemplary spacer molecule of the present invention. D: a donor region, X2 and X1: function-imparting units, PEG: a PEG region, A: a peptide acceptor region, Bio: biotin, and Fl: a fluorescent dye.

FIG. 2 shows a detailed constitution of an exemplary spacer molecule. The spacer molecule comprises a PEG region containing polyethylene glycol as a main component; a CCA region comprising puromycin or puromycin and DNA and/or RNA of at least 1 residue; a donor region containing DNA and/or RNA of at least 1 or more residues; and further a function-imparting unit (X) comprising DNA and/or RNA of which at least 1 residue of nucleotide is functionally modified. In FIG. 2, a fluorescent substance T(F1) and biotin T(Bio) are used as the function-imparting unit (X).

<2> Coding Molecule of the Present Invention

The coding molecule of the present invention is a nucleic acid comprising a 5' untranslated region comprising a transcription promoter and a translation enhancer; an ORF region that is bonded to the 3'-terminal side of the 5' untranslated region and encodes a protein; and a 3'-terminal region that is bonded to the 3'-terminal side of the ORF region and contains a polyA sequence and a sequence which a restriction enzyme XhoI recognizes on the 5'-terminal side of the polyA sequence.

The coding molecule may be DNA or RNA. In the case of RNA, the 5'-terminal end may have a Cap structure or not. Further, the coding molecule may be incorporated in an arbitrary vector or plasmid.

The 3'-terminal region contains the XhoI sequence and a polyA sequence downstream therefrom. As a factor affecting the ligation efficiency of the spacer molecule and the coding molecule, the polyA sequence in the 3'-terminal region is important. The polyA sequence is a polyA continuous chain comprising at least 2 or more residues of a mixture of dA and rA or either thereof, preferably a polyA continuous chain of 3 or more residues, more preferably 6 or more residues, further preferably 8 or more residues.

As a factor affecting translation efficiency of the coding molecule, there can be mentioned a combination of the 5' UTR comprising a transcription promoter and a translation enhancer and the 3'-terminal region containing a polyA sequence. The effect of the polyA sequence in the 3'-terminal region is usually exhibited when it comprises 10 or less residues. The transcription promoter of the 5' UTR is not particularly limited, and T7/T3, SP6 or the like can be used. SP6 can be preferably used, and when the omega sequence or a sequence containing a part of the omega sequence is used as a translation enhancer sequence, in particular, SP6 is particularly preferred. The translation enhancer is preferably a part of the omega sequence. As the part of the omega sequence, a part of the TMV omega sequence (O29; Gallie D. R. & Walbot V. (1992) Nucleic Acids Res., 20, 4631-4638) is preferred.

Further, for the translation efficiency, a combination of the XhoI sequence and the polyA sequence is important in the 3'-terminal region. Further, a combination of a sequence having an affinity tag in a portion downstream from the ORF region, i.e., upstream of the XhoI sequence, and the polyA sequence is also important. The affinity tagged sequence is not particularly limited so long as it is a sequence for using any means that can detect a protein such as an antigen-antibody reaction. A Flag-tag sequence, which is a tag for affinity separation/analysis based on an antigen-antibody reaction, is preferred. As the effect of the polyA sequence, the translation efficiency of an affinity tag such as a Flag tag having the XhoI sequence bonded thereto and further bonded with a polyA sequence is improved.

The structure effective for the translation efficiency is also effective for the assigning efficiency.

The ORF region may be any sequence comprising DNA and/or RNA. The sequence is not limited, and it may be a gene sequence, exon sequence, intron sequence or random sequence, or it can be any sequence in the natural world or any artificial sequence. Further, when SP6+O29 are used as the 5' UTR of the coding molecule, and Flag+XhoI+$A_n$ (n=8) are used as the 3'-terminal region, for example, the length of the 5' UTR is about 60 bp and that of the 3'-terminal region is about 40 bp. These are lengths that allow incorporation of them into a PCR primer as adaptor regions. Therefore, the coding molecule of the present invention having the 5' UTR and the 3'-terminal region can be readily constructed by PCR using any vector, plasmid or cDNA library. In the coding molecule of the present invention, translation may be carried out exceeding the ORF region. That is, a termination codon does not need to exist at the end of the ORF region.

Figure 3:
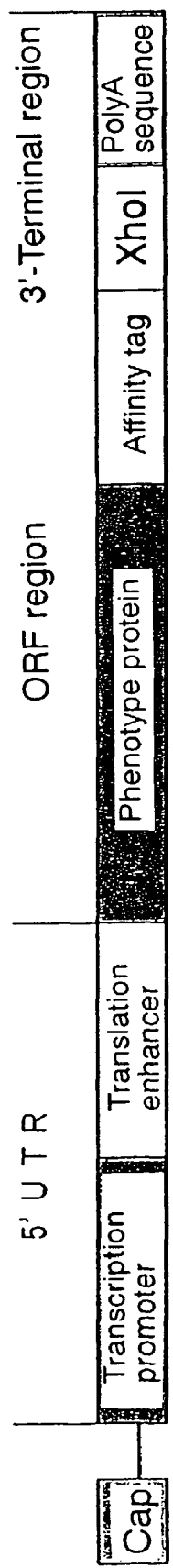
FIG. 3 shows a detailed constitution of an exemplary coding molecule of the present invention (SP6 corresponds to SEQ ID NO: 14, O29 (Omega 29) corresponds to SEQ ID NO: 15, Flag-tag corresponds to SEQ ID NO: 16).

FIG. 3 shows a detailed constitution of an exemplary coding molecule. The coding molecule comprises the 3'-terminal region; 5' UTR containing a transcription promoter and a translation enhancer comprising DNA and/or RNA; and an ORF region comprising a sequence information of a decoded portion, that is, encoding a phenotype protein. In FIG. 3, the 3'-terminal region contains an affinity tag sequence comprising DNA or RNA, XhoI sequence and polyA sequence, and a Flag-tag sequence is used. As the 5' UTR, a sequence containing SP6 as a transcription promoter and O29, which is a part of the omega sequence, as a translation enhancer is used.

<3> Genotype Molecule of the Present Invention and Method for Constructing the Same The genotype molecule of the present invention is constructed by bonding the 3'-terminal end of a coding molecule, which is a nucleic acid comprising a 5' untranslated region comprising a transcription promoter and a translation enhancer; an ORF region that is bonded to the 3'-terminal side of the 5' untranslated region and encodes a protein; and a 3'-terminal region that is bonded to the 3'-terminal side of the ORF region and comprises the polyA sequence, to a donor region of the spacer molecule of the present invention.

The coding molecule constituting the genotype molecule of the present invention is the same as described above about the coding molecule of the present invention except that the XhoI sequence is not essential in the aforementioned coding molecule of the present invention. However, it preferably to have the XhoI sequence.

The genotype molecule of the present invention can be constructed by bonding the 3'-terminal end of the aforementioned coding molecule and the donor region of the spacer molecule by an ordinary ligase reaction. As the reaction conditions, conditions of 4 to 25° C. and 4 to 48 hours can be mentioned. If polyethylene glycol having the same molecular weight as that of polyethylene glycol in the PEG region of the spacer molecule containing the PEG region is added to a reaction system, the reaction time can be reduced to 0.5 to 4 hours at 15° C.

The combination of the spacer molecule and the coding molecule has an important effect on ligation efficiency. The 3'-terminal region of the coding portion, which corresponds to an acceptor, preferably contains at least 2 or more residues, preferably 3 or more residues, more preferably 6 to 8 or more residues of the polyA sequence of DNA or RNA. Further, as the translation enhancer of 5' UTR, a partial sequence of the omega sequence (O29, FIG. 3) is preferred. As the donor region of the spacer portion, dC (deoxycytidylic acid) of at least 1 residue or dCdC (dideoxycytidylic acid) of 2 residues is preferred. This makes it possible to use RNA ligase to avoid the problems of DNA ligase and maintain 60 to 80% of the efficiency.

When the genotype molecule is RNA, it is preferable to bond (a) the 3'-terminal end of a coding molecule comprising a 5' untranslated region comprising a transcription promoter and a translation enhancer, an ORF region that is bonded to the 3'-terminal side of the 5' untranslated region and encodes a protein, and a 3'-terminal region that is bonded to the 3'-terminal side of the ORF region and comprises the polyA sequence, to (b) a donor region of the spacer molecule as defined in any one of (1) to (4) comprising RNA by using an RNA ligase in the presence of free polyethylene glycol having the same molecular weight as that of polyethylene glycol constituting the PEG region in the spacer molecule.

At the time of the ligation reaction, by adding polyethylene glycol having the same molecular weight as that of the PEG region in the spacer portion containing the PEG region, ligation efficiency can be improved to 80 to 90% or more irrespective of the molecular weight of polyethylene glycol in the spacer portion, and the separation process after the reaction can be omitted.

<4> Assigning Molecule of the Present Invention and Method for Constructing the Same The assigning molecule of the present invention is constructed by ligating the aforementioned genotype molecule of the present invention to a phenotype molecule which is a protein encoded by the ORF region in the genotype molecule, by transpeptidation.

The assigning molecule of the present invention is also constructed by translating the genotype molecule of the present invention in a cell-free translation system to ligate it to a phenotype molecule which is a protein encoded by the ORF region in the genotype molecule, by transpeptidation.

The cell-free translation system is preferably of wheat germ or rabbit reticulocyte. The translation conditions may be usually adopted conditions. For example, conditions of 25 to 37° C. and 15 to 240 minutes can be mentioned.

As for the cell-free translation system, the construction of the assigning molecules was examined in systems of *Escherichia coli* (*E. coli*), rabbit reticulocyte and wheat germ so far, and the assigning molecules were confirmed only in the rabbit reticulocyte system (Nemoto, N., Miyamoto-Sato, E., Yanagawa, H. (1997) FEBS Lett., 414, 405; Roberts, R. W.,) Szostak, J. W. (1997) Proc. Natl. Acad. Sci. USA, 94, 12297). However, according to the present invention, the assigning molecule can also be constructed in a wheat germ system as an assigning molecule having a spacer portion containing the PEG region. Further, the rabbit reticulocyte system was not so practical due to lack of stability of genotype molecule and conventionally applied only to genotype molecules having a short chain length (Roberts, R. W., Szostak, J. W. (1997) Proc. Natl. Acad. Sci. USA, 94, 12297; Nemoto, N., Miyamoto-Sato, E., Yanagawa, H. (1997) FEBS Lett., 414, 405). However, the assigning molecule of the present invention having a spacer portion containing the PEG region is more stable in the wheat germ system, and therefore the wheat germ system is a practically useful system where molecules having a long chain length can be handled.

<5> Screening Method of the Present Invention

The screening method of the present invention is a method for screening a nucleotide sequence encoding a protein that acts on a target substance, which comprises measuring interactions between a decoded portion of an assigning molecule and the target substance by using a library comprising a plurality of the assigning molecules as defined in (17), among which at least a part of the assigning molecules have different sequences of the ORF regions in their coding portions, and detecting the nucleotide sequence of the coding portion of the assigning molecule exhibiting the interaction.

The aforementioned library can be constructed according to a usual method for constructing a library comprising assigning molecules except that the assigning molecules of the present invention are used as the assigning molecules. For example, in the evolutionary molecular engineering, there can be used libraries constructed by employing the methods of Error-prone PCR (Leung, D. W., et al. (1989) J. Methods Cell Mol. Biol., 1, 11-15), Sexual PCR (Stemmer, W. P. C. (1994) Proc. Natl. Acad. Sci. USA, 91, 10747-10751), DNA shuffling, mutation library (Yanagawa, H. & Tsuji, Y. "Mutant DNA Library Construction Method"; Japanese Patent Application No. 2000-293692) and so forth. In the genome functional analysis, a cDNA library constructed by random priming, dT priming or the like can be used.

As the target substance, proteins (including peptide, antibody etc.), nucleotides and so forth can be mentioned. Interactions can be measured by a method suitable for the type of the target substance (for example, Rigaut, G. et al. (1999) Nature Biotech., 17, 1030-1032).

The nucleotide sequences can be detected by a usual method. For example, amplification by PCR or the like can be mentioned. For example, the nucleotide sequences can be amplified by RT-PCR or the like (Joyce, G. F. (1989) Gene, 82, 83; Szostak, J. W. & Ellington, A. D. (1990) Nature, 346, 818).

<6> Effect of the Present Invention

The spacer molecule of the present invention serves as a spacer portion in an assigning molecule and is an improved spacer containing polyethylene glycol as a main component compared with a conventional spacer containing DNA as a main component. This makes possible to construct the assigning molecule not only in a rabbit reticulocyte translation system but also in a wheat germ cell-free translation system, markedly improve stability of the genotype molecule in both of the translation systems, and makes any post-translation treatment unnecessary.

It is epoch-making that the construction of the assigning molecule conventionally limited to the rabbit reticulocyte cell-free translation system (Nemoto, N., Miyamoto-Sato, E., Yanagawa, H. (1997) FEBS Lett., 414, 405; Roberts, R. W., Szostak, J. W. (1997) Proc. Natl. Acad. Sci. USA, 94, 12297) can be realized in a wheat germ cell-free translation system by using a spacer comprising an PEG region (PEG) containing polyethylene glycol as a main component instead of a conventional spacer containing DNA as a main component (Liu, R., Barrick, E., Szostak, J. W., Roberts, R. W. (2000) Methods in Enzymology, 318, 268-293; Nemoto, N., Miyamoto-Sato, E., Yanagawa, H. (1997) FEBS Lett., 414, 405; Roberts, R. W, Szostak, J. W. (1997) Proc. Natl. Acad. Sci. USA, 94, 12297). Further, in comparison with those using a conventional DNA spacer (S30 spacer: Liu R., Barrick E., Szoztak J. W., Roberts, R. W. (2000) Methods in Enzymology, 318, 268-293) or a spacer of containing DNA as a main component having a polyethylene glycol molecular weight of 400 or less (F30 spacer: Liu R., Barrick E., Szoztak J. W., Roberts, R. W. (2000) Methods in Enzymology, 318, 268-293), the genotype molecule containing the spacer portion of the present invention has significantly high stability in both of the rabbit and wheat translation systems and hence does not require post-treatment after assigning translation for improving assigning efficiency. Since the treatment after the assigning translation can be simplified, the working time for the assigning translation can be shortened from 48 to 72 hours to 0.5 to 1 hour. Further, since the stability of the genotype molecule is higher in the wheat germ cell-free translation system than in the rabbit reticulocyte cell-free translation system, the stability of genotype molecule can be made higher by the spacer portion containing the PEG region (PEG) as a main component in two ways. Therefore, it becomes possible to construct a library including coding portions having a long chain length and thereby increase diversity of the library.

By introducing a fluorescent substance into nucleotide of dT as a function-imparting unit (X), the assigning molecule, which is conventionally detected by using a radioisotope (RI) with much labor and time, can be readily detected based on fluorescence. Further, the assigning molecule can be separated and purified from a cell-free protein synthesis system by introducing biotin or any of various tags.

The reason why the stability of the genotype molecule containing a spacer portion derived from the spacer molecule of the present invention is high is considered that, since the 3'-terminal side is protected by a spacer portion having polyethylene glycol with no electric charge, mRNA having the spacer portion is prevented from being attacked by nuclease from the 3'-terminal side. Further, the reason why the post-translation treatment becomes unnecessary, and the assigning molecule can be constructed not only in a rabbit reticulocyte cell-free translation system, but also in a wheat germ cell-free translation system is considered that, since a spacer containing PEG as a main component causes no interaction with ribosome, other proteins or nucleic acids included in the translation system, degree of freedom for the spacer is increased not only in the rabbit reticulocyte cell-free translation system, but also in the wheat germ cell-free translation system in comparison with a DNA spacer, and puromycin of the spacer quickly enters into the A site on ribosome to accelerate a ligation reaction between puromycin and a protein.

The coding molecule of the present invention serves as the coding portion of the assigning molecule, and specific sequences can be used for the 5'-terminal and 3'-terminal sides of the coding molecule improve translation efficiency and further improve the assigning efficiency by 4 to 5 times.

Effect of improving the translation efficiency is exhibited with a constitution comprising 5' UTR comprising a transcription promoter and a translation enhancer, comprising DNA and/or RNA; an ORF region comprising the main sequence of a decoded portion; and further a 3'-terminal region comprising the polyA sequence, comprising DNA and/or RNA. It is known that a polyA sequence stabilizes mRNA, and its average length is said to be several hundred bp in eukaryote. However, the polyA sequence having a length of 10 bp or less is particularly effective in the present invention. Further, the polyA sequence is generally a sequence contained in 3' UTR and is not translated. However, in the present invention, the polyA sequence may be translated to constitute a part of the decoded portion. Further, it is generally known that translation efficiency is improved with a full-length omega sequence as for the enhancer sequence compared with a short omega sequence (Gallie, D. R., Walbot, V. (1992) Nucleic Acids Res., 20, 4631-4638). However, in the present invention, a short omega sequence (O29 in FIG. 3) shows better translation efficiency to the contrary. The reason for such novel effect is considered that particular effects such as better stability of a genotype molecule containing the O29 sequence compared with that of a genotype molecule containing a full-length omega sequence may possibly result from a combination of the 5' UTR and the 3'-terminal region. In actual examinations, the genotype molecule was more stable when the 5' UTR contained O29 containing a part of the omega sequence rather than the full-length omega sequence.

By combining the spacer molecule and the coding molecule of the present invention, high ligation efficiency of the spacer portion can always be realized without depending on the coding portion.

As the effect that is not exhibited with the coding portion alone or the spacer portion alone, marked increase of ligation efficiency of the spacer portion and the coding portion is mentioned. The ligation efficiency of the coding portion and the spacer portion is conventionally 40% or less (Nemoto, N., Miyamoto-Sato, E., Yanagawa, H. (1997) FEBS Lett., 414, 405; Roberts, R. W., Szostak, J. W. (1997) Proc. Natl. Acad. Sci. USA, 94, 12297). However, the ligation efficiency affected by the 3'-terminal end sequence of the coding portion is always made high by the third aspect of the present invention. For the ligation reaction, a sprint and DNA ligase have been conventionally used as means for bonding a spacer and a genotype in the RNA-peptide fusion method (Roberts, R. W. & Szostak, J. W. (1997) Proc. Natl. Acad. Sci. USA, 94, 12297). However, upon transcription, 1 random residue that does not exist in a template may be often added to the 3'-terminal end of the genotype, and hence the sequence of the genotype is not complementary to the sequence of the sprint. As a result, the spacer bonding efficiency was not favorable. Further, in the in vitro virus method (Nemoto, N., Miyamoto-Sato, E., Yanagawa, H. (1997) FEBS Lett., 414, 405), RNA ligase is used as a method for bonding the spacer and the genotype. The aforementioned problems do not occur with RNA ligase since the sprint is unnecessary. However, it is known that RNA ligase originally has lower enzymatic activity compared with DNA ligase, and its spacer bonding efficiency was also unfavorable. For use of RNA ligase as a ligation enzyme, there are known nucleotides desirable and undesirable for the nucleotide sequence acceptor and the donor nucleotide sequence (Uhlenbeck, O. C., Gumport, R. I. (1982) The Enzymes, vol. XV, 31-58; England, T. E., Uhlenbeck, O. C. (1978) Biochemistry 17, 2069-2076; Romaniuk, E., McLaughlin, L. W., Neilson, T., Romaniuk, P. J. (1982) Eur. J. Biochem., 125, 639-643). However, all of these experiments were conducted by using those with short chains, and no report has shown that high ligation efficiency is always obtained with a long acceptor or donor as in the present invention.

As for the reason why the ligation efficiency is improved by the present invention, it is known that the longer the donor side nucleic acid becomes, the lower the ligation efficiency becomes when RNA ligase or DNA ligase is used (Uhlenbeck, O. C. & Gumport, R. I. (1982) The Enzymes, vol. XV, 31-58). Therefore, it is possible that a high ligation efficiency similar to that of ligation with nucleic acid (donor) having a short chain length is achieved by using polyethylene glycol with no electric charge instead of DNA as a main component of the spacer, and using dC of 1 residue (deoxycytidylic acid) or dCdC (dideoxycytidylic acid) of 2 residues are contained in the donor region. However, the efficiency may decline depending on the sequence of the 3α-terminal end sequence region of the coding portion, but this problem was solved by providing the polyA sequence in the 3'-terminal region. This sequence also contributes to the improvement of translation efficiency. A ligation efficiency of 60 to 80% or higher can be obtained by the using a polyA sequence irrespective of sequences upstream therefrom. Further, when the molecular weight of polyethylene glycol of the PEG region is increased, the ligation efficiency may decline. However, as to this problem, the ligation efficiency of 80 to 90% or higher can be obtained, irrespective of the molecular weight of polyethylene glycol, by adding polyethylene glycol having the same molecular weight as that of the PEG region in the spacer portion and, in particular, adjusting the mixing ratio of the coding portion and the spacer portion in the ligation reaction. It is considered that the ligation reaction of the 3'-terminal end of the coding portion and the 5'-terminal end of the spacer portion is promoted because viscosity in the reaction field is increased due to the existence of polyethylene glycol. As described above, since sufficiently high ligation efficiency is obtained, separation treatment conducted after the reaction in the ligation process becomes unnecessary, and conventional working time of 48 to 72 hours (Nemoto, N., Miyamoto-Sato, E., Yanagawa, H. (1997) FEBS Lett., 414, 405) was shortened to 4 to 8 hours. Consequently, it becomes possible to efficiently and readily construct a large-scale library. Further, assigning efficiency is markedly improved by further using the constitution of 5' UTR in the coding portion.

Thus, contrary to the conventional theory (Liu, R., Barrick, E., Szostak, J. W., Roberts, R. W. (2000) Methods in Enzymology, 318, 268-293), the inventors of the present invention practically realized a large-scale library with higher diversity not only in a rabbit reticulocyte cell-free translation system, but also in a wheat germ cell-free translation system.

EXAMPLES

Hereafter, examples of the assigning molecules of the present invention will be specifically described. However, the following examples are construed as being an aid for obtaining concrete knowledge of the present invention, but in no way limit the scope of the present invention.

Example 1

The spacer molecule and the coding molecule shown in FIG. 1 were ligated by a ligation reaction to construct a genotype molecule comprising a spacer portion derived from the spacer molecule and a coding portion derived from the coding molecule, and this genotype molecule and a phenotype molecule were ligated via puromycin on ribosome by assigning translation to prepare an assigning molecule comprising the coding portion and spacer portion derived from the genotype molecule and a decoded portion derived from the phenotype molecule. Details will be described below.

(1) Synthesis of Spacer Molecule Containing PEG Region

Figure 11:
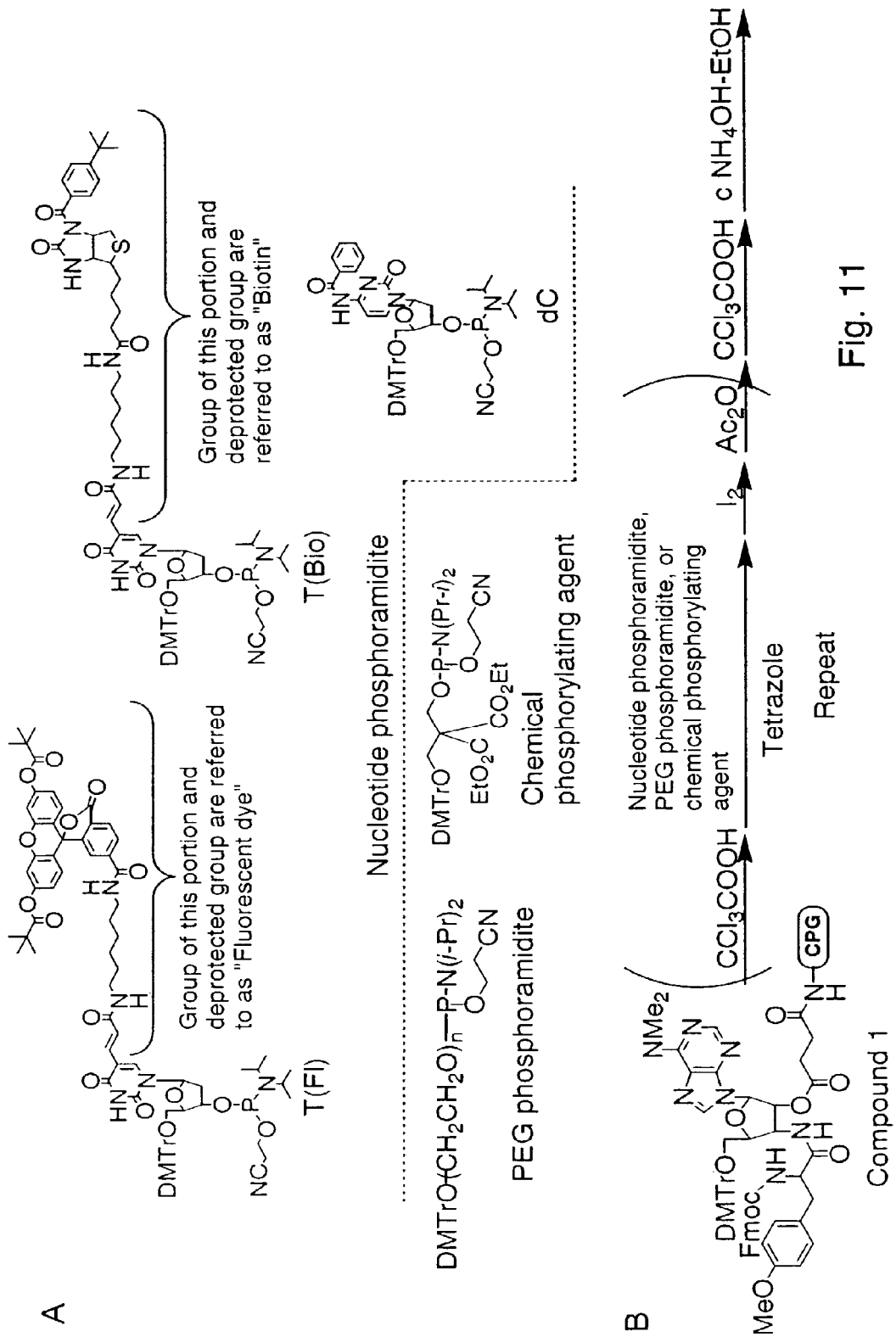
FIG. 11 shows a synthesis scheme of the spacer molecule of the present invention. A shows a structure of a compound used for synthesis, and B shows synthesis steps.

The spacer molecule containing a PEG region was synthesized by using the method outlined in FIG. 11, B. Compound 1 was synthesized by the method reported by Ikeda et al. (Ikeda, S. et al. (1998) Tetrahedron Lett., 39, 5975-5978). The structures of the used nucleotide phosphoramidites (phosphoramidites providing dC, T(F1) and T(Bio)), PEG phosphoramidite and chemical phosphorylating agent are shown in FIG. 11, A. The nucleotide phosphoramidites and the chemical phosphorylating agent were purchased from Glen Research (Virginia, USA). Polyethylene glycol (PEG) having average molecular weights of 1000, 2000 and 3000 were purchased from NOF Corporation (Tokyo, Japan). PEG having an average molecular weight of 4000 was purchased from Furka (Switzerland). PEG phosphoramidites were synthesized by the method reported by Jaschke et al. (Jaschke, A. et al. (1993) Tetrahedron Lett., 34, 301-304). In FIG. 11, DMTr represents 4,4'-dimethoxytrityl group, and Fmoc represents 9-fluorenemethoxycarbonyl group.

The following treatments A to D were performed for Compound 1 (400 mg, containing 10 µmol of puromycin residue) according to a predetermined sequence until a predetermined number of nucleotides and PEG were introduced.

A. Add 1 mL of 3% trichloroacetic acid solution in methylene chloride, and leave it room temperature for 3 minutes and then wash it 3 times with 5 mL of methylene chloride. Repeat the same procedure, and then wash the reaction product 5 times with 5 mL of anhydrous acetonitrile.

B. Add, 30 µmol of nucleotide phosphoramidite, PEG phosphoramidite or chemical phosphorylating agent, 100 µL of 0.457 M tetrazole solution in anhydrous acetonitrile and 1 mL of anhydrous acetonitrile and shake it at room temperature for 15 minutes. Wash the reaction product 5 times with 5 mL of acetonitrile.

C. Add 1 mL of 50 mM iodine solution (tetrahydrofuran/pyridine/water=75:20:5), and leave it at room temperature for 3 minutes and wash 3 times with 5 mL of pyridine. Repeat the same procedure, and then wash it the reaction product 5 times with 5 mL of anhydrous pyridine.

D. Add 1 mL of 10% anhydrous acetic acid solution in pyridine and a catalytic amount of 4,4-dimethylaminopyridine, and leave it at room temperature for 20 minutes and wash it 5 times with 5 mL of pyridine and 5 times with 5 mL of methylene chloride.

To the Compound 1 to which a predetermined number of nucleotides and PEG are introduced according to a predetermined sequence by the above treatments, 1.5 mL of concentrated aqueous ammonia and 0.5 mL of ethanol were added and the mixture was shaken at room temperature for 14 hours. A solid phase carrier (CPG) was removed by filtration, and the filtrate was lyophilized. The residue was purified by HPLC [column: YMC pack ODS-A SH-343-5 produced by YMC (Kyoto, Japan), eluent: a linear concentration gradient of 10 to 60% acetonitrile in 0.1 M aqueous triethylammonium acetate (pH 7.0) over 30 minutes, flow rate: 10 mL/min] to obtain a spacer molecule containing a PEG region.

The types and yields of the obtained spacer molecules containing a PEG region were as follows. Meanings of the abbreviations are as follows; p: phosphorus group, dC: deoxycytidine, PEG (number): PEG having an average molecular weight represented by the number, Puro: puromycin, T(F1): thymidine labeled with a fluorescent dye, T(Bio): thymidine labeled with biotin.

p(dCp)$_2$PEG(1000)p(dCp)$_2$Puro, yield 8.7%
p(dCp)$_2$T(F1)pPEG(1000)pdCpPuro, yield: 62%
p(dCp)$_2$T(F1)pPEG(1000)p(dCp)$_2$Puro, yield: 14%
p(dCp)$_2$PEG(2000)p(dCp)$_2$Puro, yield: 7%
p(dCp)$_2$T(F1)pPEG(2000)pdCpPuro, yield: 30%
p(dCp)$_2$T(F1)pPEG(2000)p(dCp)$_2$Puro, yield: 27%
p(dCp)$_2$T(Bio)pPEG(2000)pdCpPuro, yield: 9%
p(dCp)$_2$T(Bio)pPEG(2000)p(dCp)$_2$Puro, yield: 8%
p(dCp)$_2$T(Bio)pT(F1)pPEG(2000)pdCpPuro, yield: 2%
p(dCp)$_2$T(Bio)pT(F1)pPEG(2000)p(dCp)$_2$Puro, yield: 8%
p(dCp)$_2$PEG(3000)pdCpPuro, yield: 2%
p(dCp)$_2$PEG(3000)p(dCp)$_2$Puro, yield: 22%
p(dCp)$_2$T(F1)pPEG(3000)pdCpPuro, yield: 29%
p(dCp)$_2$T(F1)pPEG(3000)p(dCp)$_2$Puro, yield: 23%
p(dCp)$_2$T(F1)pPEG(4000)pdCpPuro, yield: 16%
p(dCp)$_2$T(F1)pPEG(4000)p(dCp)$_2$Puro, yield: 17%

(2) Preparation of Coding Molecule

A coding molecule was amplified by PCR using a DNA template containing the sequence of the mouse-derived c-jun (Gentz, R., Rauscher, F. J. 3d, Abate, C., Curran, T. (1989) Science, 243, 1695-9; Neuberg, M., Schuermann, M., Hunter, J. B., Muller, R. (1989) Nature, 338, 589-90). At this time, 12 types of DNA templates in total were prepared by using 6 types of primers (SP6-O29, T7-O29, SP6-AO, T7-AO, T7-O', T7-K) for the 5'-terminal end and 6 types of primers (FlagXA, FlagX, FlagXA(G3), FlagXA(C1), FlagA, Flag) for the 3'-terminal side. That is, PCR was performed 4 times for each DNA template under the following conditions by using TaKaRa Ex Taq (Takara Shuzo), and purification was performed by using QIAquick PCR Purification Kit (QIAGEN).

TABLE 1

| (PCR reaction solution) | |
|---|---|
| 10 × Ex Buffer | 10 µl |
| 2.5 mM dNTP | 8 µl |
| DEPC water | 76.7 µl |
| Ex Taq | 0.3 µl |
| Template (1 nmol/µl) | 1 µl |
| Primer 1 (20 pmol/µl) | 2 µl |
| Primer 2 (20 pmol/µl) | 2 µl |
| Total | 100 µl |

TABLE 2

| | (Template, primers and reaction conditions) | | |
|---|---|---|---|
| Template: | c-jun[F] | (SEC ID NO: 1) | |
| Primer 1: | 5' SP6-O29 | (SEC ID NO: 2) | SP6 + partial omega sequence (O29) |
| | 5' T7-O29 | (SEC ID NO: 3) | T7 + partial omega sequence (O29) |
| | 5' SP6-AO | (SEC ID NO: 4) | SP6 + full-length omega sequence |
| | 5' T7-AO | (SEC ID NO: 5) | T7 + full-length omega sequence |
| | 5' T7-O' | (SEC ID NO: 6) | T7 + partial omega sequence (O') not overlapping O29 |
| | 5' T7-K | (SEC ID NO: 7) | T7 + Kozak sequence |
| Primer 2: | 3' FlagXA | (SEC ID NO: 8) | Flag + modified XhoI site + polyA |
| | 3' FlagX | (SEC ID NO: 9) | Flag + modified XhoI site |
| | 3' FlagXA(G3) | (SEC ID NO: 10) | Flag + modified XhoI site + polyA |
| | 3' FlagXA(C1) | (SEC ID NO: 11) | Flag + modified XhoI site + polyA |
| | 3' FlagA | (SEC ID NO: 12) | Flag + polyA |
| | 3' Flag | (SEC ID NO: 13) | Flag |
| Program: | 94° C. 2 min | | |
| | 35 cycles of the following | | |
| | 94° C. | 30 sec | |
| | 62° C. | 30 sec | |
| | 74° C. | 1 min | |

6 to 12 µg of the following coding molecules (DNA templates) were obtained by the above method. For convenience, the coding molecules were designated as "(name of Primer 1)Jun-(name of Primer 2)" according to the primers used for PCR. DNA or RNA is indicated in the brackets.

[DNA] SP6-O29Jun-FlagXA, yield: 10 μg
[DNA] T7-O29Jun-FlagXA, yield: 12 μg
[DNA] SP6-AOJun-FlagXA, yield: 10 μg
[DNA] T7-AOJun-FlagXA, yield: 7 μg
[DNA] T7-O'Jun-FlagXA, yield: 9 μg
[DNA] T7-KJun-FlagXA, yield: 10 μg
[DNA] SP6-O29Jun-FlagX, yield: 7 μg
[DNA] SP6-O29Jun-FlagXA(G3), yield: 8 μg
[DNA] SP6-O29Jun-FlagXA(C1), yield: 6 μg
[DNA] SP6-O29Jun-FlagA, yield: 10 μg
[DNA] SP6-O29Jun-Flag, yield: 10 μg Subsequently, RNA templates (=coding molecules) were prepared from DNA templates by transcription. That is, the above-obtained DNA templates were transcribed (37° C., 2 hours) under the following conditions by using RiboMAXTM Large Scale RNA Production Systems (Promega), and purification was performed by using RNeasy Mini Kit (QIAGEN).

TABLE 3

(Transcription reaction solution)

| | |
|---|---|
| 5 × SP6 buffer | 10 μl |
| Nucleotide mixture (ATP/MTP/CTP), 25 mM | 10 μl |
| GTP, 10 mM | 7.5 μl |
| Cap Analog (m7G(5')ppp(5')G), 40 mM | 9.4 μl |
| DNA template | 1 μg |
| SP6 enzyme mixture | 5 μl |
| RNase-free water | Remainder |
| Total | 50 μl |

By the above method, 250 to 500 pmol of the following coding molecules (RNA templates) were obtained.
[RNA] SP6-O29Jun-FlagXA, yield: 450 pmol
[RNA] T7-O29Jun-FlagXA, yield: 350 pmol
[RNA] SP6-AOJun-FlagXA, yield: 400 pmol
[RNA] T7-AOJun-FlagXA, yield: 500 pmol
[RNA] T7-O'Jun-FlagXA, yield: 350 pmol
[RNA] T7-KJun-FlagXA, yield: 500 pmol
[RNA] SP6-O29Jun-FlagX, yield: 250 pmol
[RNA] SP6-O29Jun-FlagXA(G3), yield: 300 pmol
[RNA] SP6-O29Jun-FlagXA(C1), yield: 350 pmol
[RNA] SP6-O29Jun-FlagA, yield: 400 pmol
[RNA] SP6-O29Jun-Flag, yield: 400 pmol (3) Translation of Coding Molecule
(3-1) Translation Reaction in Wheat Germ Cell-free Translation System The coding molecules (RNA templates) were translated (26° C., 60 minutes) under the following conditions by using Wheat Germ Extract (Promega). Along with the translation, proteins were labeled (Miyamoto-Sato, E., Nemoto, N., Kobayashi, K., and Yanagawa, H. (2000) Nucleic Acids Res., 28, 1176-1182; Nemoto, N., Miyamoto-Sato, E. and Yanagawa, H. (1999) FEBS Lett., 462, 43-46). Electrophoresis was performed by 17.5% SDS-PAGE, and fluorescence of fluorescein in the bands was measured by using a multi-format image analyzer, Molecular Imager FX (Bio-Rad).

TABLE 4

(Translation reaction solution)

| | |
|---|---|
| Amino acid mixture, 1 mM | 0.8 μl |
| 1 M Potassium | 0.76 μl |
| RNase inhibitor, 10 U/μl | 0.8 μl |
| RNA template (coding molecule) | 4 pmol |
| Wheat Germ Extract (Promega) | 5 μl |
| Fluoro-dCpPuro, 400 μM | 0.6 μl |

TABLE 4-continued (Translation reaction solution)

| | |
|---|---|
| RNase-free water | Remainder |
| Total | 10 μl |

Jun proteins having a molecular weight of about 25 kDa were obtained from the coding molecules (RNA templates) by the above method and quantified by image analysis. The Jun proteins obtained from the respective coding molecules were designated as shown in the following table.

TABLE 5

| Coding molecule (RNA template) | Jun protein |
|---|---|
| (a) [RNA] SP6-O29Jun-FlagXA | p-SP6-O29 = p-FXA |
| (b) [RNA] T7-O29Jun-FlagXA | p-T7-O29 |
| (C) [RNA] SP6-AOJun-FlagXA | p-SP6-AO |
| (d) [RNA] T7-AOJun-FlagXA | p-T7-AO |
| (e) [RNA] T7-OJun-FlagXA | p-T7-O' |
| (f) [RNA] T7-KJun-FlagXA | p-T7-K |
| (g) [RNA] SP6-O29Jun-FlagX | p-FX |
| (h) [RNA] SP6-O29Jun-FlagXA(G3) | p-FX'A |
| (i) [RNA] SP6-O29Jun-FlagXA(C1) | p-FX"A |
| (j) [RNA] SP6-O29Jun-FlagA | p-FA |

Figure 7:
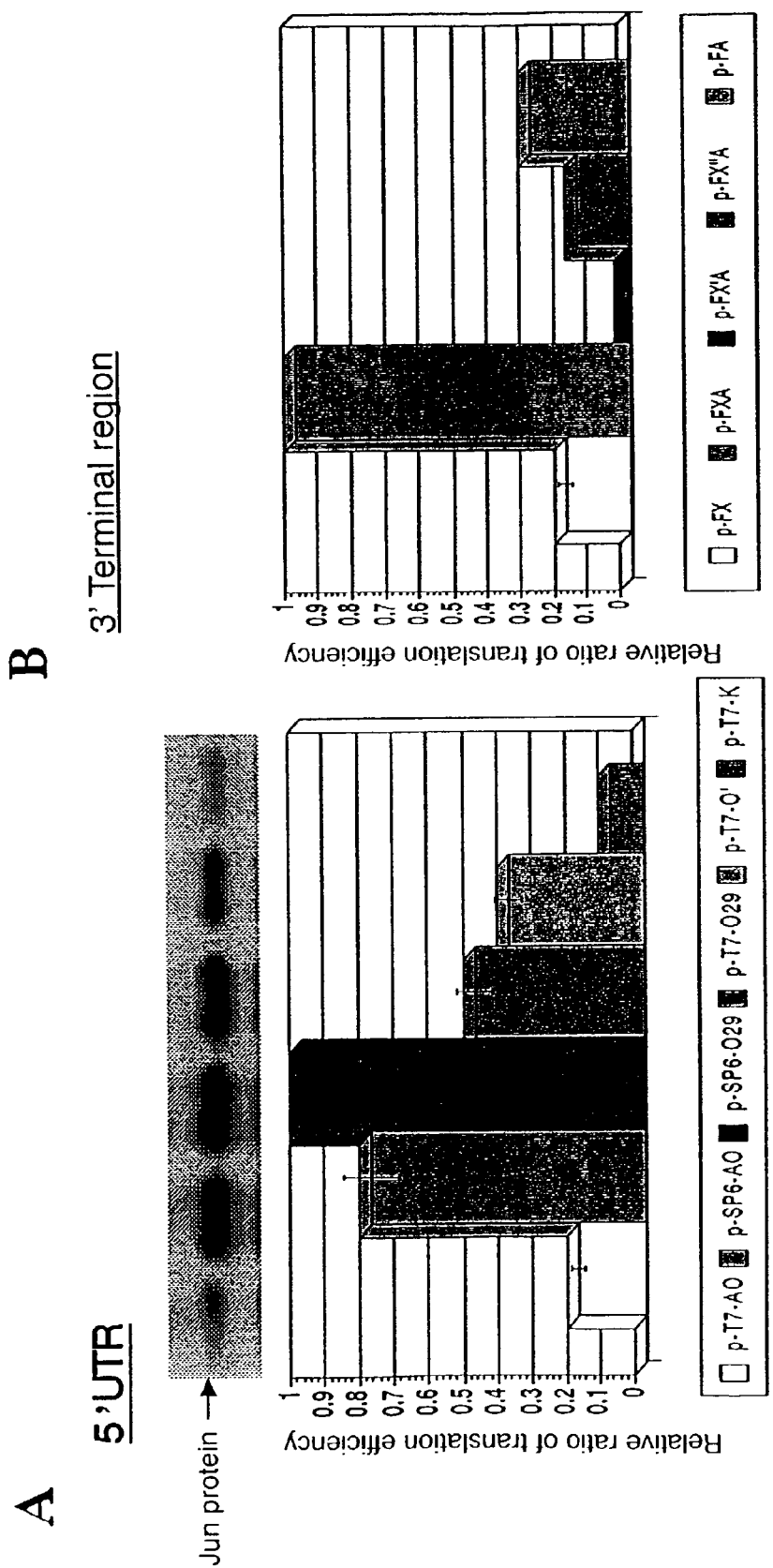
FIG. 7 shows changes in translation efficiency by optimization of the coding molecule of the present invention. A: optimization of 5' UTR (the result of electrophoresis (photograph) is also shown), and B: optimization of the 3'-terminal region (3' tail).

FIG. 7, A shows the results of comparison of the above (a) to (f) about efficiency (relative rate) of translation into the-Jun proteins. These results indicate that translation efficiency became high when 5' UTR contained a transcription promoter (SP6) of SP6 RNA polymerase as a transcription promoter (p-SP6-AO and p-SP6-O29) and when it contained a part of tobacco mosaic virus TMV omega (O29) as an enhancer sequence (p-SP6-O29 and p-T7-O29), and that translation efficiency became particularly high when both were contained (p-SP6-O29).

FIG. 7, B shows the results of comparison of the above (a) and (g) to (j) about efficiency of translation into the Jun proteins. These results indicate that translation efficiency became high when the polyA sequence was contained in the 3'-terminal region (p-FA), and when the polyA sequence and the XhoI sequence were contained in the 3'-terminal region. (p-FXA). That is, the translation efficiency is significantly different when the XhoI sequence bonded to a Flag tag and the same further bonded with the polyA sequence are compared. Further, as effect of the combination of the XhoI sequence and the polyA sequence, translation efficiency for the Flag tag bonded with XhoI sequence and polyA sequence is much higher than that for the Flag tag bonded with only the polyA sequence. Further, since substitution of 1 residue in the XhoI sequence showed strong influence, the XhoI sequence itself is also important.

(4) Ligation of Spacer Molecule and Coding Molecule

A spacer molecule containing a PEG region and a coding molecule (RNA template) were ligated (15° C., 20 hours) under the following conditions by using T4 RNA ligase (Takara Shuzo) and purified by using RNeasy Mini Kit (QIAGEN). The ligation product (genotype molecule of c-jun) was subjected to electrophoresis by 8 M Urea 4%

PAGE, and fluorescence of ethidium bromide (EtBr) and fluorescein in the molecule were detected by using a multi-format image analyzer, Molecular Imager FX (Bio-Rad). Further, similar detection was performed for the spacer molecules and the coding molecules of G2 and G4 by changing the ligation conditions to 15° C. and 4 hours and adding free PEG having the same molecular weight as that of PEG in the PEG region to the ligation reaction mixture or without adding it. Detection for the G4 molecule was further performed by changing the amount of the spacer molecules to 40 nmol and the amount of the free PEG to 80 nmol.

TABLE 6

| (Ligation reaction solution) | |
| --- | --- |
| Spacer molecule containing PEG | 20 nmol |
| (Free PEG | 60 nmol, when free PEG is added) |
| RNA template (coding molecule) | 50 pmol |
| 10x buffer | 5 μl |
| 0.1 M DTT | 1.5 μl |
| 40 mM ATP | 0.5 μl |

TABLE 6-continued

| (Ligation reaction solution) | |
| --- | --- |
| DMSO | 10 μl |
| ESA | 3 μl |
| RNase inhibitor | 1 μl |
| T4 RNA ligase | 10 μl |
| RNase-free water | Remainder |
| Total | 50 μl |

The following genotype molecules, which were ligation products of various spacer molecules and coding molecules, were obtained by the above method with ligation efficiency of 20 to 95%.

The ligation efficiency is a relative ratio of the band intensity of the genotype molecules based on the total of band intensity of coding molecules and band intensity of genotype molecules taken as 100%. The band intensities were analyzed by using a multi-format image analyzer for the bands obtained by electrophoresis of the molecules by 8 M Urea 4% SDS-PAGE, followed by ethidium bromide staining of the nucleic acids in the gel.

TABLE 7

| Spacer molecule | Coding molecule | Genotype molecule |
| --- | --- | --- |
| p(dCp)2T(Fl)pPEG(1000)p(dCp)2Puro | [RNA] SP6-O29Jun-FlagXA | G1 |
| p(dCp)2T(Fl)pPEG(2000)p(dCp)2Puro | [RNA] SP6-O29Jun-FlagXA | G2 |
| p(dCp)2T(Fl)pPEG(3000)p (dCp)2Puro | [RNA] SP6-O29Jun-FlagXA | G3 |
| p(dCp)2T(Fl)pPEG(4000)p(dCp)2Puro | [RNA] SP6-O29Jun-FlagXA | G4 |
| p(dCp)2T(Fl)pPEG(1000)pdCpPuro | [RNA] SPG-O29Jun-FlagXA | G5 |
| p(dCp)2T(Fl)pPEG(2000)pdCpPuro | [RNA] SP6-O29Jun-FlagXA | G6 |
| p(dCp)2T(Fl)pPEG(3000)pdCpPuro | [RNA] SP6-O29Jun-FlagXA | G7 |
| p(dCp)2T(Fl)pPEG(4000)pdCpPuro | [RNA] SP6-O29Jun-FlagXA | G8 |
| p(dCp)2PEG(1000)p(dCp)2Puro | [RNA] SP6-O29Jun-FlagXA | G9 |
| p(dCp)2PEG(2000)p(dCp)2Puro | [RNA] SP6-O29Jun-FlagXA | G10 |
| p(dCp)2PEG(3000)p(dCp)2Puro | [RNA] SP6-O29Jun-FlagXA | G11 |
| p(dCp)2PEG(3000)pdCpPuro | [RNA] SP6-O29Jun-FlagXA | G12 |
| p(dCp)2T(Bio)pPEG(2000)pdCpPuro | [RNA] SP6-O29Jun-FlagXA | G13 |
| p(dCp)2T(Bio)pPEG(2000)p(dCp)2Puro | [RNA] SP6-O29Jun-FlagXA | G14 |
| p(dCp)2T(Bio)pT(Fl)pPEG(2000)pdCpPuro | [RNA] SP6-O29Jun-FlagXA | G15 |
| p(dCp)2T(Bio)pT(Fl)pPE G(2000)p(dCp)2Puro | [RNA] SPG-O29Jun-FlagXA | G16 |
| p(dCp)2T(Fl)pPEG(2000)p(dCp)2Puro | [RNA] SP6-O29JunFlagXA | G17 (=G2) |
| p(dCp)2T(Fl)pPEG(2000)p(dCp)2Puro | [RNA] T7-O29Jun-FlagXA | G18 |
| p(dCp)2T(Fl)pPEG(2000)p(dCp)2Puro | [RNA] SP6-AOJun-FlagXA | G19 |
| p(dCp)2T(Fl)pPEG(2000)p(dCp)2Puro | [RNA] T7-AOJunFlagXA | G20 |
| p(dCp)2T(Fl)pPEG(2000)p(dCp)2Puro | [RNA] T7-O'JunFlagXA | G21 |
| p(dCp)2T(Fl)pPEG(2000)p(dCp)2Puro | [RNA] T7-KJun-FlagXA | G22 |
| p(dCp)2T(Fl)pPEG(2000)p(dCp)2Puro | [RNA] SP6-O29Jun-FlagX | G23 |
| p(dCp)2T(Fl)pPEG(2000)p(dCp)2Puro | [RNA] SP6-O29Jun-FlagXA(G3) | G24 |
| p(dCp)2T(Fl)pPEG(2000)p (dCp)2Puro | [RNA] SP6-O29Jun-FlagXA(C1) | G25 |

TABLE 7-continued

| Spacer molecule | Coding molecule | Genotype molecule |
|---|---|---|
| p(dCp)2T(Fl)pPEG(2000)p(dCp)2Puro | [RNA] SP6-O29JunFlagA | G26 |
| p(dCp)2T(FI)pPEG(2000)p(dCp)2Puro | [RNA] SP6-O29Jun-Flag | G27 |

TABLE 8

Figure 9:
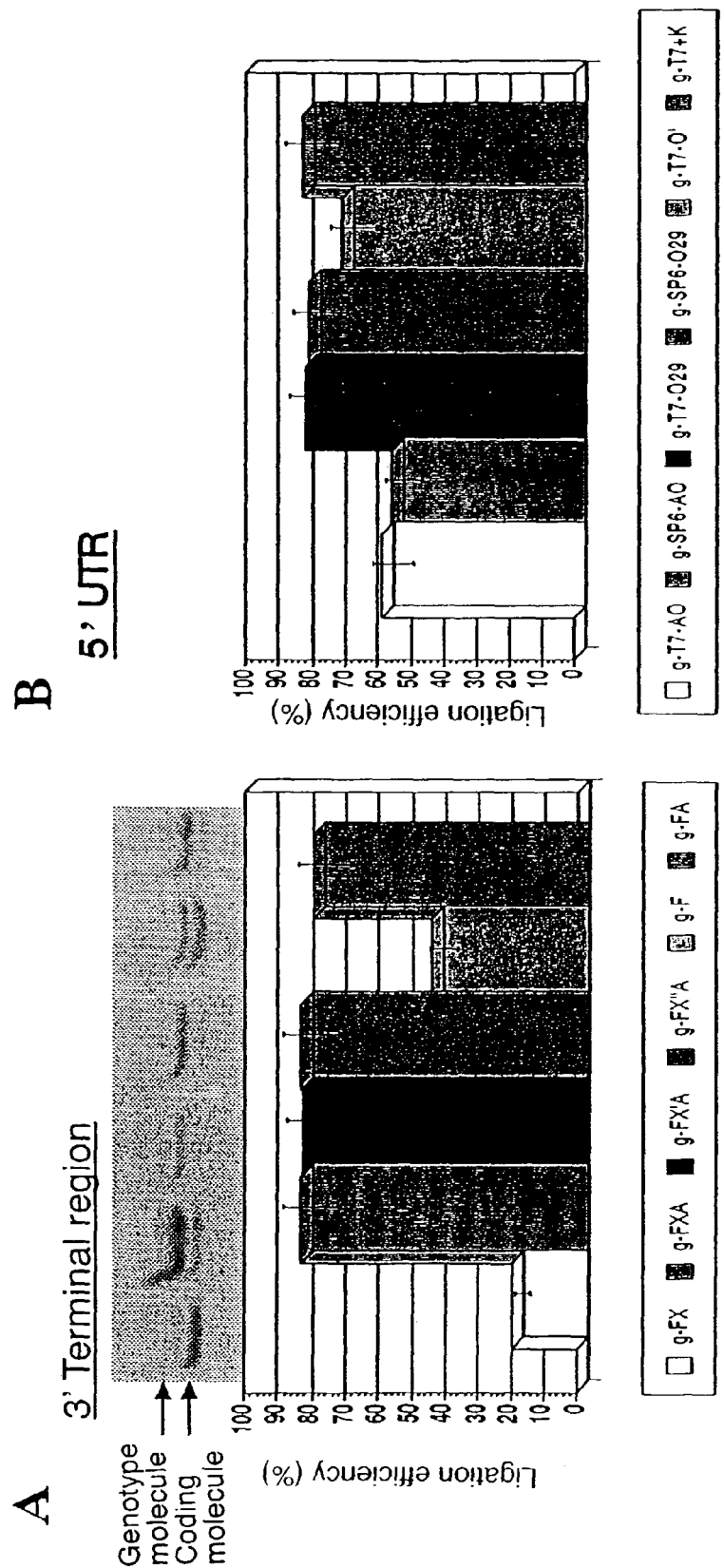
FIG. 9 shows changes in ligation efficiency resulting from optimization of the coding molecule of the present invention. A: optimization of the 3'-terminal region (3' tail) (the result of electrophoresis (photograph) is also shown), and B: optimization of 5' UTR.
Figure 10:
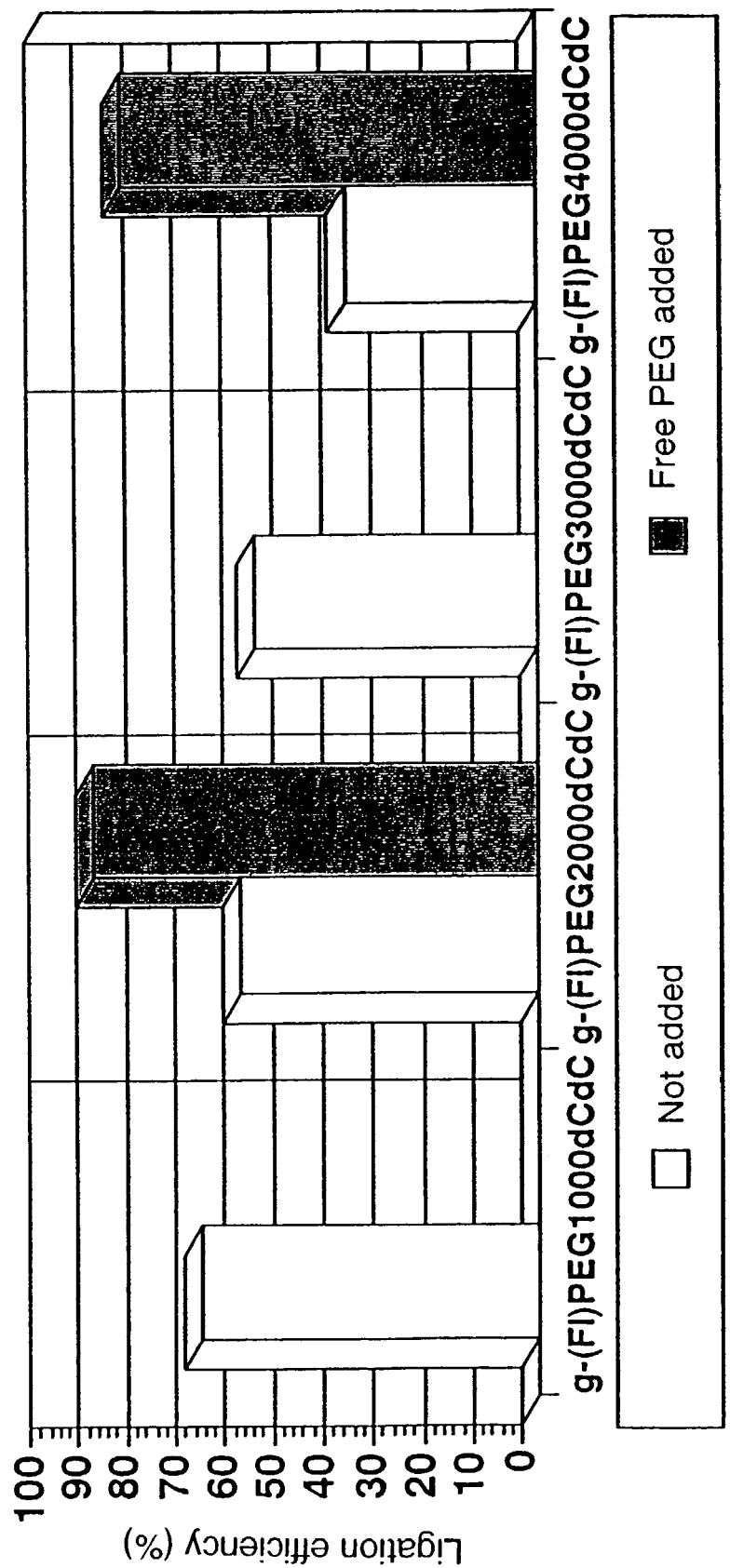
FIG. 10 shows changes in ligation efficiency depending on the molecular weight of the PEG region in the spacer molecule of the present invention.

| Genotype molecule | |
|---|---|
| G1: g-(F1)PEG(1000)dCdC | See FIG. 10 for efficiency. |
| G2: g-(F1)PEG(2000)dCdC | See FIG. 10 for efficiency. |
| G3: g-(F1)PEG(3000)dCdC | See FIG. 10 for efficiency. |
| G4: g-(F1)PEG(4000)dCdC | Efficiency: 73% (see FIG. 10 efficiency when amounts of spacer molecule and free PEG are changed) |
| G5: g-(F1)PEG(1000)dC | Efficiency: 75% |
| G6: g-(F1)PEG(2000)dC | Efficiency: 64% |
| G7: g-(F1)PEG(3000)dC | Efficiency: 58% |
| G8: g-(F1)PEG(4000)dC | Efficiency: 40% |
| G9: g-PEG(1000)dCdC | Efficiency: 98% |
| G10: g-PEG(2000)dCdC | Efficiency: 90% |
| G11: g-PEG(3000)dCdC | Efficiency: 85% |
| G12: g-PEG(3000)dC | Efficiency: 84% |
| G13: g(Bio)PEG(2000)dC | Efficiency: 85% |
| G14: g-(Bio)PEG(2000)dCdC | Efficiency: 83% |
| G15: g-(Bio)(F1)PEG(2000)dC | Efficiency: 75% |
| G16: g-(Bio)(F1)PEG(2000)dCdC | Efficiency: 78% |
| G17(=G2): g-(F1)PEG(2000)dCdC(gSP6 O29=g-FXA) | See FIG. 9 for efficiency. |
| G18: g-(F1) PEG(2000) dCdC(g-T7-O29) | See FIG. 9 for efficiency. |
| G19: g-(F1)PEG(2000)dCdC(gSP6-AO) | See FIG. 9 for efficiency. |
| G20: g-(F1)PEG(2000)dCdC(g-T7-AO) | See FIG. 9 for efficiency. |
| G21: g-(F1)PEG(2000)dCdC(g-T7-O') | See FIG. 9 for efficiency. |
| G22: g-(F1)PEG(2000)dCdC(g-T7-K) | See FIG. 9 for efficiency. |
| G23: g-(FI)PEG(2000)dCdC(g-FX) | See FIG. 9 for efficiency. |
| G24: g-(F1)PEG(2000)dCdC(gFX'A) | See FIG. 9 for efficiency. |
| G25: g-(FI)PEG(2000)dCdC(g-FX"A) | See FIG. 9 for efficiency. |
| G26: g-(F1)PEG(2000)dCdC(gFA) | See FIG. 9 for efficiency. |
| G27: g-(FI)PEG(2000)dCdC(gF) | See FIG. 9 for efficiency. |

FIG. 9, A shows the results of comparison of efficiencies for G23 (g-FX), G17 (g-FXA), G24 (g-FX'A), G25 (g-FX"A), G27 (g-F) and G26 (g-FA). FIG. 9, B shows the results of comparison of efficiencies for G20 (g-T7-AO), G19 (g-SP6-AO), G18 (g-T7-O29), G17 (g-SP6-O29), G21 (g-T7-O') and G22 (g-T7-K).

As shown in FIG. 9, A, high ligation efficiency was obtained when a polyA sequence was contained in the 3'-terminal region. The ligation efficiency of the coding molecule and the spacer molecule was conventionally 40% or lower (Nemoto, N., Miyamoto-Sato, E., Yanagawa, H. (1997) FEBS Lett., 414, 405; Roberts, R. W. & Szostak, J. W. (1997) Proc.

Natl. Acad. Sci. USA, 94, 12297). However, ligation efficiency affected by the 3'-terminal end sequence of the coding portion is made high by adopting the 3'-terminal region containing a polyA sequence. Further, as shown in FIG. 9, B, high ligation efficiency of 60 to 80% can be obtained thanks to the polyA sequence irrespective of sequences upstream thereof.

FIG. 10 shows comparison with experiments for G2 and G4 where free PEG having the same molecular weight as that of PEG in the PEG region was added.

Although the ligation efficiency tended to decline as the molecular weight of polyethylene glycol in the PEG region increased ("Not added" in FIG. 10), ligation efficiency was improved by adding free PEG having the same molecular weight as PEG in the PEG region upon the ligation reaction irrespective of the molecular weight of PEG in the spacer molecule (90% for G2 and 73% for G4 when the spacer molecule is 20 nmol), and the separation process after the reaction could be omitted.

Further, the ligation efficiency was further improved by adjusting the mixing ratio of the coding molecules and the spacer molecules in the ligation reaction mixture (85% for G4), and hence the ligation efficiency as high as 80 to 90% was obtained irrespective of the molecular weight of polyethylene glycol ("free PEG added" in FIG. 10).

(5) Construction of Assigning Molecule (5-1) Assigning Translation in Wheat Germ Cell-free Translation System Wheat Germ Extract (Promega) was used as a wheat germ cell-free translation system, and Rabbit Reticulocyte Lysate System (Promega) was used as a rabbit reticulocyte cell-free translation system. The c-jun genotype molecules obtained by the above ligation were added to each of the translation systems to perform assigning translation, and the assigning molecules were subjected to electrophoresis by 8 M Urea 11% SDS-PAGE and detected based on fluorescence of fluorescein by using a multi-format image analyzer, Molecular Imager FX (Bio-Rad). No post-translation treatment was performed, and the undiluted solution from the translation system was subjected to the electrophoresis.

TABLE 9

| Rabbit reticulocyte cell-free translation system: 30° C., 30 min | |
|---|---|
| Amino acid mixture, 1 Mm | 0.2 μl |
| RNase inhibitor, 20 U/μl | 0.4 μl |
| Genotype (spacer portion + coding portion) | 2 pmol |
| Rabbit Reticulocyte Lysate | 7.0 μl |
| RNase-free water | Remainder |
| Total | 10 μl |

TABLE 10

| Wheat germ cell-free translation system: 26° C., 30 min | |
|---|---|
| Amino acid mixture, 1 mM | 0.8 μl |
| 1 M Potassium | 0.76 μl |
| RNase inhibitor, 10 U/μl | 0.8 μl |
| Genotype (spacer portion + coding portion) | 2 pmol |
| Wheat Germ Extract | 5.0 μl |
| RNase-free water | Remainder |
| Total | 10 μl |

The following assigning molecules comprising various c-jun genotypes and the phenotypes thereof were obtained with assigning efficiency of 4 to 60% by the above method.

The assigning efficiency is a relative ratio of the fluorescence intensity of the assigning molecules based on the total of the band intensity of genotype molecules and the band intensity of assigning molecules taken as 100%. The molecules were subjected to electrophoresis by 8 M Urea 4% SDS-PAGE, and fluorescence intensity of the bands of the genotypes and fluorescence intensity of the assigning molecules were analyzed by using a multi-format image analyzer.

TABLE 11

| Genotype molecule | Assigning molecule |
|---|---|
| G1: g-(Fl)PEG(1000)dCdC | v-(Fl)PEG(1000)dCdC |
| G2: g(Fl)PEG(2000)dCdC | v-(Fl)PEG(2000)dCdC |
| G3: g-(Fl)PEG(3000)dCdC | v-(Fl)PEG(3000)dCdC |
| G4: g-(Fl)PEG(4000)dCdC | v-(Fl)PEG(4000)dCdC |
| G5: g-(Fl)PEG(1000)dC | v-(Fl)PEG(1000)dC |
| G6: g-(Fl)PEG(2000)dC | v-(Fl)PEG(2000)dC |
| G7: g(Fl)PEG(3000)dC | v-(Fl)PEG(3000)dC |
| G8: g-(Fl)PEG(4000)dC | v-(Fl)PEG(4000)dC |
| G17: g-(Fl)PEG(2000)dCdC(wSP6O29) | v-(Fl)PEG(2000)dCdC(v-SP6-O29) |
| G18: g-(Fl)PEG(2000)dCdC(gTTO29) | v-(Fl)PEG(2000)dCdC(v-T7-O29) |
| G19: g-(Fl)PEG(2000)dCdC(gSP6AO) | v-(Fl)PEG(2000)dCdC(v-SP6-AO) |
| G20: g-(Fl)PEG(2000)dCdC(wT7AO) | v-(Fl)PEG(2000)dCdC(v-T7-AO) |
| G21: g-(Fl)PEG(2000)dCdC(gT7O') | v-(Fl)PEG(2000)dCdC(v-T7O') |
| G22: g-(Fl)PEG(2000)dCdC(gT7K) | v-(Fl)PEG(2000)dCdC(v-T7-K) |

Figure 4:
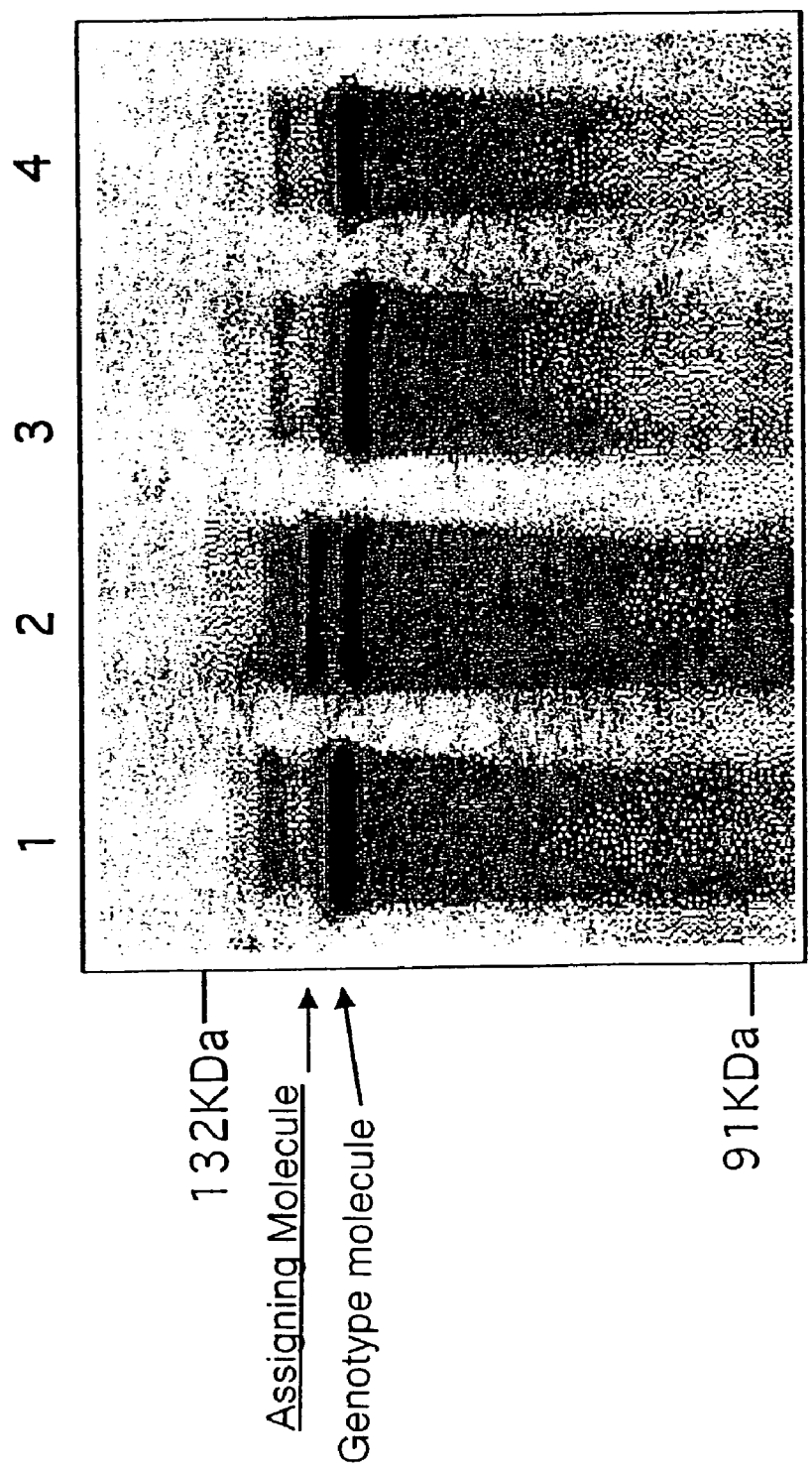
FIG. 4 shows results (electrophoresis photograph) of construction of the assigning molecules of the present invention in a wheat germ cell-free translation system.

FIG. 4 shows the results of the assigning translation using the assigning molecule of G2 (=G17). Lane 1 represents a genotype molecule, Lane 2 represents a product of assigning translation of the genotype molecule in the wheat germ cell-free translation system, Lane 3 represents a product obtained by adding 20 µM puromycin as a protein synthesis inhibitor under the same conditions as those used for Lane 2, and Lane 4 represents a product obtained by decomposing the protein with protease K after the reaction for Lane 2.

The assigning molecule was observed only in Lane 2. This indicates that the assigning molecule was constructed by translation in the wheat germ cell-free translation system. This also indicates that detection is possible without post-treatment after the translation.

Further, it is shown that assigning molecules conventionally detected with RI requiring much labor and time can be readily detected with fluorescence by using genotype molecules containing a spacer portion with a fluorescent substance introduced into the function-imparting unit (X).

(5-2) Stability of Assigning Molecule

Figure 5:
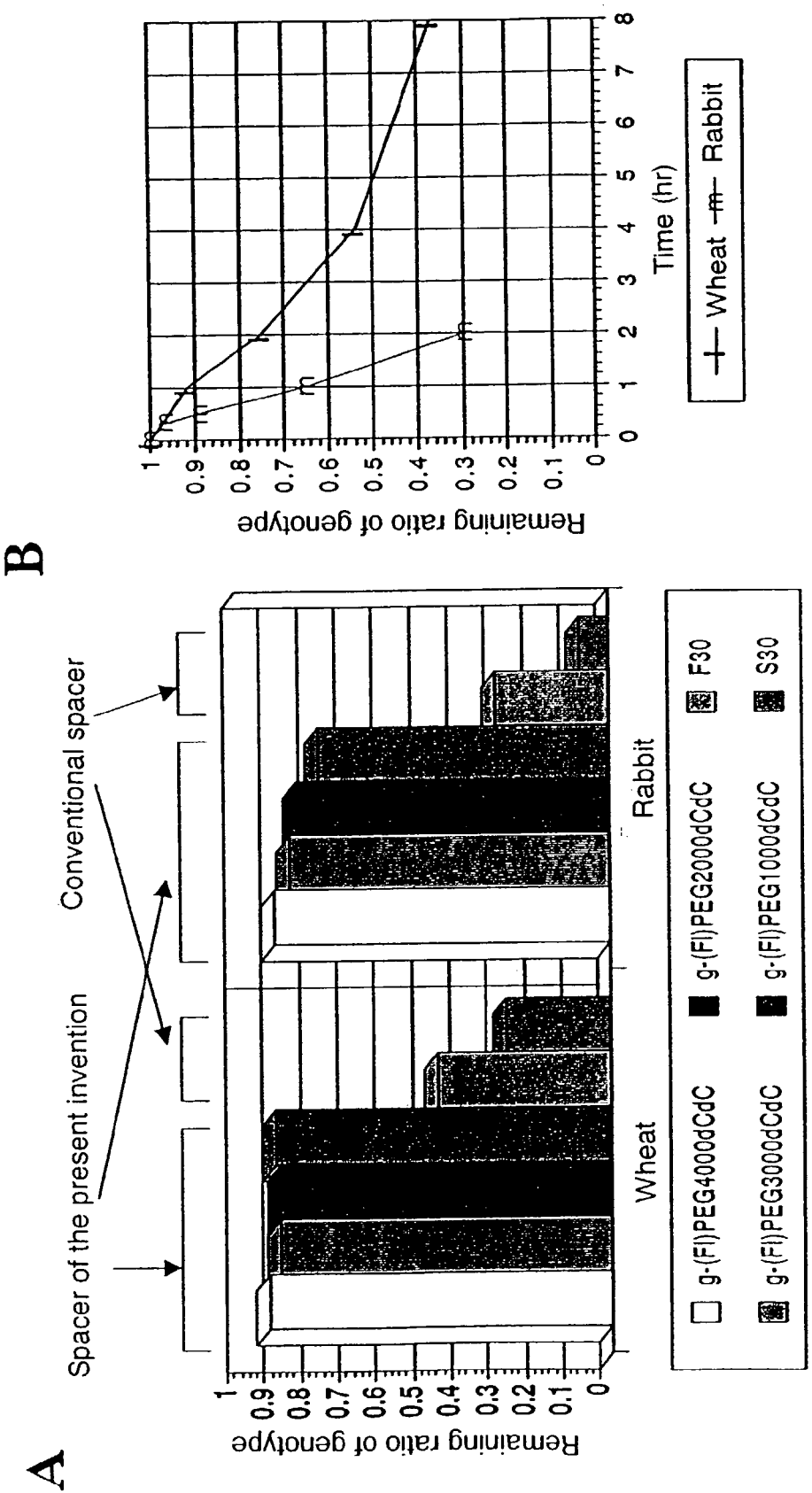
FIG. 5 shows stability of the genotype molecules of the present invention (ligation product of the spacer molecule and the coding molecule). A: comparison of stability of genotype molecules with different spacers, and B: comparison of stability of the genotype molecules of the present invention in the different translation systems.

Stability of genotype molecule containing the spacer of the present invention, and that of genotype molecules containing the following conventional spacers were compared in the wheat germ and rabbit reticulocyte cell-free translation systems. The experiment conditions were the same as in the above (5-1) except that translation was performed at 30° C. for 20 minutes in the rabbit system and at 26° C. for 20 minutes in the wheat system in the presence of 20 µM puromycin as the translation inhibitor. The results are shown in FIG. 5, A. The numerical values in the graph represent the ratios of the remaining genotype molecules based on the amount before translation as a reference.

The coding molecules, the spacer molecules and the genotype molecules used in this experiment are shown below.

Therefore, post-treatment after the assigning translation conventionally required to improve assigning efficiency becomes unnecessary. Since treatment after the assigning translation can be simplified, working time for assigning translation can be shortened from 48 to 72 hours to 0.5 to 1 hour.

Further, it was observed that stability of the genotype tended to increase as the molecular weight of polyethylene glycol increased. The stability was favorable with PEG having a molecular weight of 1000 or more, and the genotype had almost the same property as that of the DNA spacer and was unstable with PEG having a molecular weight of 400 or less (FIG. 5, A).

Further, the stability of the genotype of the present invention was compared in the wheat germ and rabbit reticulocyte cell-free translation systems. The experiment conditions were the same as in the above (5-1) except that translation was performed in the presence of 20 µM puromycin as translation inhibitor at 30° C. for 0.25, 0.5, 1 and 2 hours in the rabbit system and at 26° C. for 1, 2, 4 and 8 hours in the wheat system. The genotype molecule used in this experiment was G17=G2 [g-(F1)PEG(2000)dCdC(g-SP6-O29)]. The results are shown in FIG. 5, B. Numerical values in the graph represent the ratios of the remaining genotype molecules based on the amount before the translation as a reference.

It can be seen that the stability of the genotype molecule was higher in the wheat germ cell-free translation system than in the rabbit reticulocyte cell-free translation system (FIG. 5, B). Since a spacer portion containing a PEG region as a main component makes a genotype molecule more stable especially in the wheat germ cell-free translation system, it becomes possible to construct a library including coding portions with a long chain length by using genotype molecules containing such a spacer portion, and hence a library with high diversity can be obtained.

TABLE 12

| Coding molecule | Spacer molecule | Genotype molecule |
|---|---|---|
| [RNA] SP6-O29Jun-FlagXA | p(dCp)$_2$T(F1)pPEG(3000)p(dCp)$_2$Puro | G2 |
| [RNA] SP6-O29Jun-FlagXA | p(dCp)$_2$T(FI)pPEG(2000)p(dCp)2Puro | G3 |
| [RNA] SP6-O29Jun-FlagX | p(F1)(dAp)$_{21}$[C9]$_3$dAp(dCp)$_2$Puro | 30F |
| [RNA] SP6O29Jun-FlagX | p(F1)(dAp)$_{27}$(dCp)$_2$Puro | 30S |

G2: g-(F1)PEG(3000)dCdC

G3: g-(F1)PEG(3000)dCdC

30F: g-(dAp)$_{21}$(F1)[C9]$_3$dCdC

30S: g-(dAp)$_{21}$(F1)(dAp)hd 6dCdC

It can be seen that the genotype molecules containing the spacer portion of the present invention showed significantly higher stability in both of the rabbit and wheat translation systems in comparison with those using the conventional DNA spacer (S30 spacer: Liu R., Barrick E., Szoztak J. W., Roberts, R. W. (2000) Methods in Enzymology, 318, 268-293) or the spacer containing DNA as a main component with polyethylene glycol having a molecular weight of 400 or less (F30 spacer: Liu R., Barrick E., Szoztak J. W., Roberts, R. W. (2000) Methods in Enzymology, 318, 268-293) (FIG. 5, A).

(5-3) Optimization of Acceptor Region and PEG Region

Figure 6:
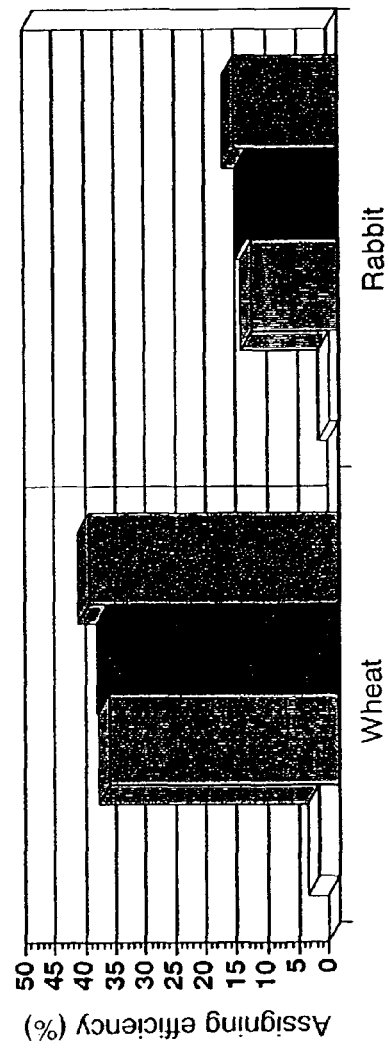
FIG. 6 shows changes in assigning efficiency by optimization of the acceptor region and the PEG region in the spacer molecule of the present invention. A: the case where the acceptor portion is dc-puromycin, and B: the case where the acceptor portion is dCdC-puromycin.
Figure 6:
Figure 6:
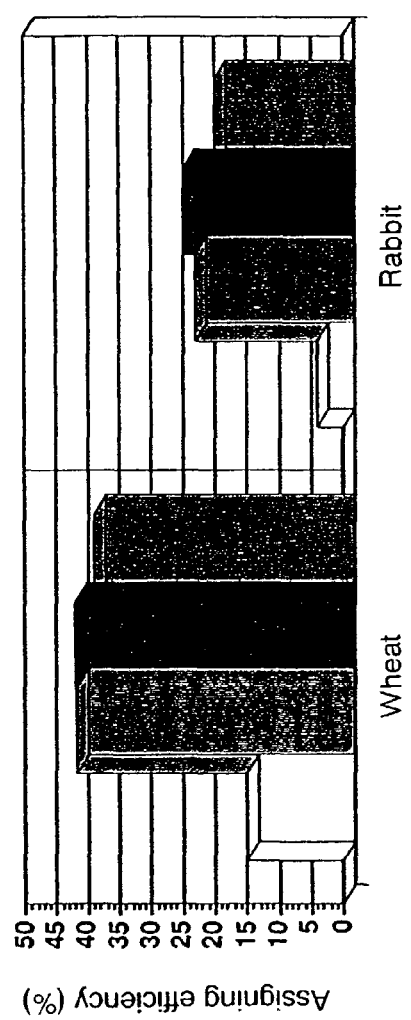
Figure 6:
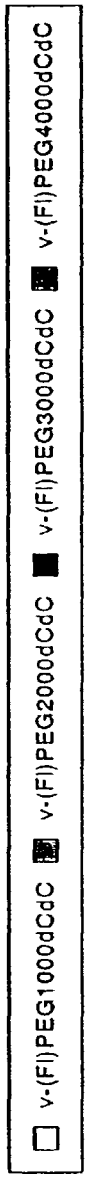

In order to optimize the acceptor region and the PEG region of the spacer molecule of the present invention, construction efficiency of the assigning molecules was compared in the wheat germ and rabbit reticulocyte cell-free translation systems. The experiment conditions were the same as described above except that the acceptor region had a constitution of dC-puromycin, spacer molecules containing the PEG regions having molecular weights of 1000, 2000, 3000 and 4000 were used, and translation was performed at 30° C. for 0.5 hours in the rabbit system and at 26° C. for 0.5 hours in the wheat system. The results are shown in FIG. 6, A. The assigning efficiency was calculated by the aforementioned method. The genotype molecules and the assigning molecules used in this experiment were G5 to G8.

Further, the results of the experiment conducted under the same conditions except that the acceptor region had the constitution of dCdC-puromycin are shown in FIG. 6, B. The genotype molecules and the assigning molecules used in this experiment were G1 to G4.

As shown in FIG. 6, it was found that, for a spacer portion having puromycin and dC (deoxycytidine) sequence of 1 residue in its acceptor region, polyethylene glycol should preferably have a molecular weight of 1000 or more, more preferably 2000 or more, further preferably 4000 or more (FIG. 6, A). It was also found that, for a spacer portion having puromycin and the dCdC sequence in its acceptor region, the effect was exhibited with polyethylene glycol having a molecular weight of 1000 or more, and it was more preferably 2000 or more, further preferably 2000 to 4000 (FIG. 6, B).

(5-4) Optimization of 5' UTR

Figure 8:
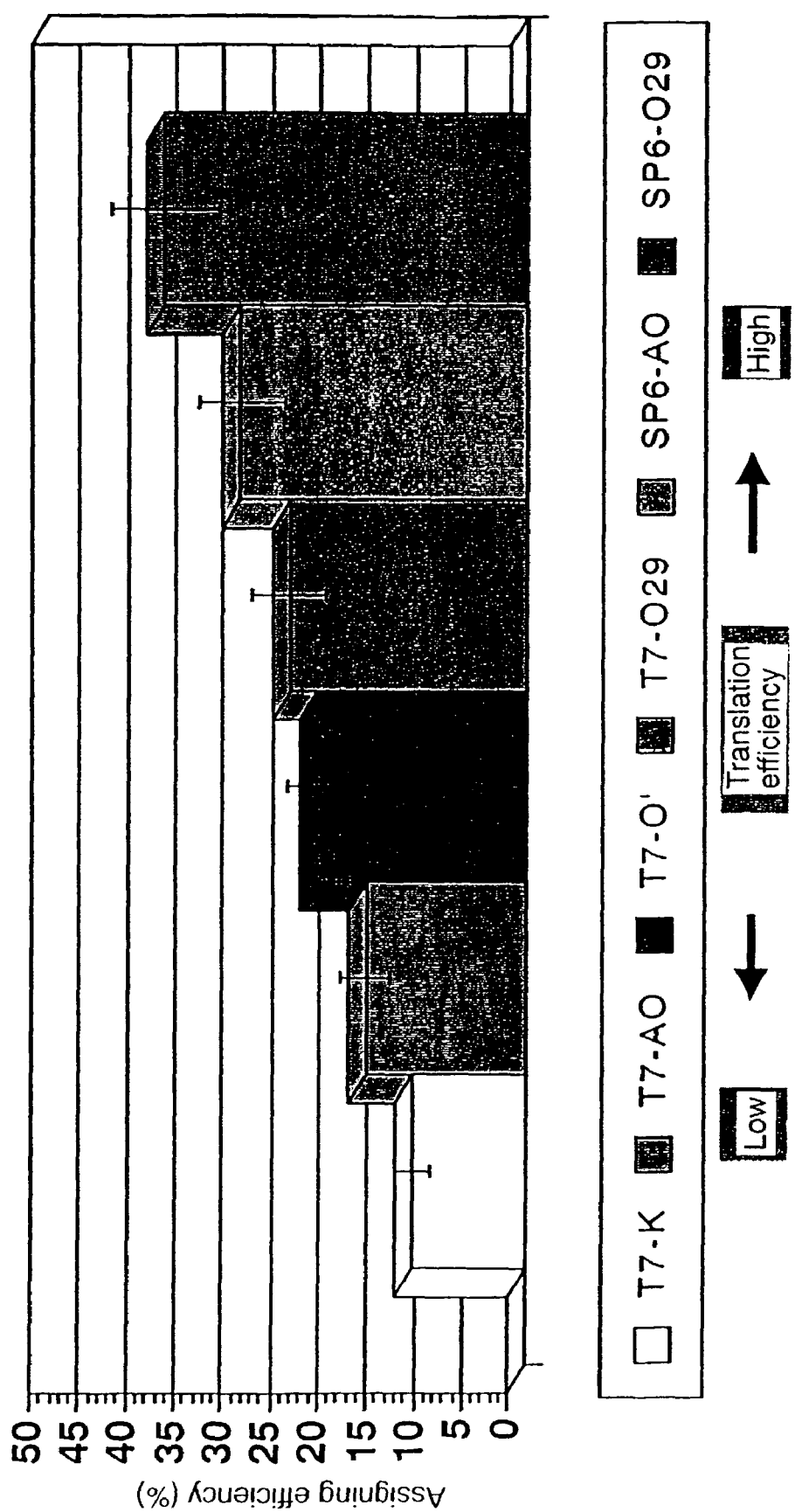
FIG. 8 shows the relationship between translation efficiency and assigning efficiency of the coding molecule of the present invention.

In order to investigate the influence of the translation efficiency of the coding portion of the present invention on the assigning efficiency, assigning molecules were constructed by using genotype molecules containing coding portions having 5' UTR with different translation efficiency, and their construction efficiency was compared. The experiment conditions were the same as in the above (5-1) except that assigning translation was performed at 26° C. for 0.5 hours in the wheat germ cell-free translation system. The results are shown in FIG. 8. The assigning efficiency was calculated in the same manner as described in the above (5-3). The genotype molecules and the assigning molecules used in this experiment were G17 to G22.

From the result shown in FIG. 8, it can be seen that the transcription promoter (SP6) of SP6 RNA polymerase is more preferred than T7 as a transcription promoter, and that a partial sequence of the omega sequence (O29) is preferred as a translation enhancer.

Further, from the result shown in FIGS. 7 and 8, it was found that the translation efficiency of the coding portion showed positive correlations with the assigning efficiency, and that the translation efficiency of the coding portion had improved. Thus, it became clear that the assigning efficiency had been improved. Therefore, it can be considered that the components contributing to the improvement of the translation efficiency also contribute to the improvement of the translation efficiency also for the 3'-terminal end sequence.

(6) Size of Library Using Assigning Molecule of the Present Invention

Size of a library using the assigning molecules of the present invention in a unit volume was calculated. As the calculation method, the absolute amount of the assigning molecules in 1 ml was calculated from the concentration of the genotype molecules, the ratio of remaining genotype molecules and the construction efficiency of the assigning molecules, and it was considered as the size of the library. The experiment conditions were the same as in the above (5-1) except that translation was performed at 26° C. for 1 hour in the wheat system and at 30° C. for 0.5 hours in the rabbit system. The results are shown in the following table. The genotype molecule and the assigning molecule used in this experiment were G17 (=G2).

TABLE 13

| Genotype concentration (nM) | Assigning efficiency (%) | Assigning molecule (pmol) | Library × $10^{13}$/ml |
|---|---|---|---|
| Wheat germ | | | |
| 100 | 57 | 52 | 3.1 |
| 200 | 51 | 94 | 5.6 |
| 400 | 37 | 136 | 8.2 |
| 800 | 21 | 155 | 9.3 |
| 1600 | 10 | 147 | 8.8 |
| 1.0 hour, ligation efficiency: 70%, genotype remaining ratio: 0.92 | | | |
| Rabbit reticulocyte | | | |
| 100 | 32 | 28 | 1.7 |
| 200 | 23 | 41 | 2.5 |
| 400 | 14 | 50 | 3.0 |
| 800 | 5 | 36 | 2.2 |
| 0.5 hour, ligation efficiency: 70%, genotype remaining ratio: 0.89 | | | |

As clearly seen from the results shown in the above table, the construction efficiency of the assigning molecules was improved from 0%, to 50 to 60% in the wheat germ cell-free translation system and from 10% or lower, to 20 to 30% in the rabbit reticulocyte cell-free translation system. Further, the scale of the library was improved from 0/ml (construction was impossible) to $10^{14}$/ml in the wheat germ cell-free translation system and from $10^{12}$/ml to $10^{13}$/ml in the rabbit reticulocyte cell-free translation system.

Further, although the rabbit reticulocyte system was not so practical due to lack of stability of genotype molecule and conventionally applied only to genotype molecules having a short chain length (Roberts, R. W. & Szostak, J. W. (1997) Proc. Natl. Acad. Sci. USA, 94, 12297; Nemoto, N., Miyamoto-Sato, E., Yanagawa, H. (1997) FEBS Lett., 414, 405), it can be seen from the results shown in FIGS. 4 and 5 and the above table that an assigning molecule having a spacer portion containing a PEG region is more stable in the wheat germ system, and that the wheat germ system using such an assigning molecule is a practically useful system where long chain lengths can be can handled.

INDUSTRIAL APPLICABILITY

A coding molecule having a long chain length can be handled in a wheat germ translation system by using the molecule of the present invention. That is, a practically useful assigning translation system is provided.

What is claimed is:

1. A spacer molecule comprising a donor region which can be bonded to a 3'-terminal end of nucleic acid, a polyethylene glycol (PEG) region that is bonded to the donor region and comprises polyethylene glycol as a main component and a peptide acceptor region which is bonded to the PEG region and comprises a member selected from the group consisting of puromycin, 3'-N-aminoacylpuromycin aminonucleoside, and 3'-N-aminoacyladenosine aminonucleoside, wherein the donor region is deoxycytidylic acid or dideoxycytidylic acid, 5'-terminal end of the donor region being monophosphated, and wherein the PEG region is bonded to the donor region directly or via one or two residues of functionally modified deoxyribonucleotide or ribonucleotide.

2. A genotype molecule constructed by bonding a 3'-terminal end of a coding molecule to a 5'-terminal end of a donor region of a spacer molecule,
wherein said coding molecule is a nucleic acid comprising a 5' untranslated region comprising a transcription promoter and a translation enhancer; an open reading frame (ORF) region which is bonded to the 3'-terminal side of the 5' untranslated region and encodes a protein; and a 3'-terminal region that is bonded to the 3'-terminal side of the ORF region and comprises a polyA sequence, wherein the 3'-terminal region comprises a sequence which a restriction enzyme XhoI recognizes on the 5'-terminal end side of the polyA sequence; and wherein said spacer molecule comprises the donor region, a polyethylene glycol (PEG) region that is bonded to the donor region and comprises polyethylene glycol as a main component and a peptide acceptor region which is bonded to the PEG region and comprises a member selected from the group consisting of puromycin, 3'-N-aminoacylpuromycin aminonucleoside, and 3'-N-aminoacyladenosine aminonucleoside, wherein the donor region is deoxycytidylic acid or dideoxycytidylic acid and wherein the PEG region is bonded to the donor region directly or via one or two residues of functionally modified deoxyribonucleotide or ribonucleotide.

3. The genotype molecule according to claim 2, wherein the transcription promoter is a promoter of SP6 RNA polymerase.

4. The genotype molecule according to claim 2, which comprises an affinity tag sequence in a portion downstream from the ORF region.

5. The genotype molecule according to claim 4, wherein the affinity tag sequence is a Flag-tag sequence, which is a tag for affinity separation and analysis based on an antigen-antibody reaction.

6. An assigning molecule constructed by ligating the genotype molecule as defined in claim 2 to a phenotype molecule which is a protein encoded by the ORF region in the genotype molecule, by transpeptidation.

* * * * *